US012672834B2

(12) United States Patent
Tajima

(10) Patent No.: US 12,672,834 B2
(45) Date of Patent: Jul. 7, 2026

(54) MEDICAL IMAGE ACQUISITION APPARATUS, MAMMOGRAPHY APPARATUS, AND CONTROL PROGRAM

(71) Applicant: FUJIFILM Corporation, Tokyo (JP)

(72) Inventor: Takashi Tajima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 177 days.

(21) Appl. No.: 18/815,377

(22) Filed: Aug. 26, 2024

(65) Prior Publication Data

US 2025/0072850 A1     Mar. 6, 2025

(30) Foreign Application Priority Data

Aug. 29, 2023     (JP) ................................. 2023-139274

(51) Int. Cl.
| | |
|---|---|
| *A61B 6/12* | (2006.01) |
| *A61B 6/00* | (2006.01) |
| *A61B 6/04* | (2006.01) |
| *A61B 6/50* | (2024.01) |

(52) U.S. Cl.
CPC .............. *A61B 6/12* (2013.01); *A61B 6/0414* (2013.01); *A61B 6/502* (2013.01); *A61B 6/54* (2013.01)

(58) Field of Classification Search
None
See application file for complete search history.

(56) References Cited

U.S. PATENT DOCUMENTS

| | | |
|---|---|---|
| 2009/0299218 A1 | 12/2009 | Holler et al. |
| 2010/0054402 A1 | 3/2010 | Fischer et al. |
| 2013/0158388 A1* | 6/2013 | Blevis ................ A61B 10/0233 |
| | | 600/424 |
| 2014/0100524 A1* | 4/2014 | Zarei Mahmoodabadi .................. |
| | | A61M 5/427 |
| | | 604/116 |
| 2016/0310215 A1 | 10/2016 | Palma et al. |
| 2020/0187895 A1* | 6/2020 | Gong ................... A61B 8/5207 |
| 2021/0401381 A1 | 12/2021 | Wells et al. |
| 2022/0096024 A1* | 3/2022 | Fujimoto ............. A61B 6/0414 |
| 2025/0064434 A1* | 2/2025 | Konno ............... A61B 10/0233 |

FOREIGN PATENT DOCUMENTS

| | | |
|---|---|---|
| JP | 2010-194194 A | 9/2010 |
| JP | 2022-502138 A | 1/2022 |

* cited by examiner

*Primary Examiner* — Marcus H Taningco
(74) *Attorney, Agent, or Firm* — Studebaker Brackett PLLC

(57) ABSTRACT

A medical image acquisition apparatus including: a biopsy apparatus; an imaging table that is used to capture an image of a living body disposed on an imaging surface with an imaging apparatus; a projector that projects the image; and at least one processor, wherein the processor performs control of projecting relevant information associated with each execution stage of a biopsy that is performed on the living body using the biopsy apparatus, from the projector toward the imaging surface of the imaging table for each execution stage.

13 Claims, 9 Drawing Sheets

MEDICAL IMAGE ACQUISITION APPARATUS, MAMMOGRAPHY APPARATUS, AND CONTROL PROGRAM

CROSS-REFERENCE TO RELATED APPLICATIONS

This application claims priority from Japanese Application No. 2023-139274, filed on Aug. 29, 2023, the entire disclosure of which is incorporated herein by reference.

BACKGROUND

Technical Field

The present disclosure relates to a medical image acquisition apparatus, a mammography apparatus, and a control program.

Related Art

A biopsy is performed at a medical institution to collect a biological tissue from a living body of a patient, and a biopsy may be performed on the collected biological tissue.

US2016/0310215A discloses a biopsy method including a step of executing a tomosynthesis scan on a part of an object, a step of reconstructing a tomosynthesis scan result on a display screen such that a marker is visible and deciding a position of a lesion on the basis of the marker, a step of correlating the position of the lesion with the marker, and a step of proposing a puncture point of a biopsy tool by using a correlation between the position of the lesion and the marker.

JP2022-502138A discloses an imaging system including an X-ray tube head; a support arm; a compression system that is coupled to the support arm to be rotatable independently relative to the X-ray tube head and that includes a compression paddle, a support platform, and an X-ray receptor; and a light assembly that is coupled to the support arm, is disposed above the compression paddle, and is configured to direct one or more beams of light toward the support platform.

US2010/0054402A discloses a mammography apparatus that creates a virtual mask in which a region as a biopsy target is marked from an X-ray image of a breast, and that indicates a disposing position of the breast such that the marked region comes to a puncture position.

JP2010-194194A discloses a biopsy site extraction device that detects a lesion part in an object to be examined in at least two images, calculates a three-dimensional position of the lesion part by associating the lesion part in one image with the lesion part in the other image in a case where the lesion part in one image and the lesion part in the other image are the same lesion part, determines whether or not a biopsy needle can be inserted into the lesion part to collect a biological tissue of the lesion part, and extracts the lesion part as a biopsy site candidate in a case where the biological tissue can be collected.

US2009/0299218A discloses a mammography apparatus including a laser device that projects a position mark onto an examination target.

Since the biopsy is for puncturing a patient with a biopsy needle in front of the patient, it is preferable to perform the biopsy as quickly as possible and without making a mistake in the procedure in order to suppress a burden and fear of the patient.

Therefore, in the medical image acquisition apparatus for the biopsy, relevant information associated with a technique of the biopsy may be displayed to notify the medical worker during the operation.

However, the displayed related information may include, for example, relevant information to be referred to by the medical worker in the next execution stage of the biopsy. Therefore, there is inconvenience that the medical worker has to find the relevant information regarding the current execution stage of the biopsy from the displayed relevant information, which may affect the technique of the medical worker.

SUMMARY

The present disclosure has been made in consideration of such circumstances, and an object of the present disclosure is to provide a medical image acquisition apparatus, a mammography apparatus, and a control program which can improve an execution accuracy of a biopsy as compared with a case where relevant information associated with a technique regarding the biopsy is provided to a medical worker who performs the biopsy, regardless of the execution stage of the biopsy.

A medical image acquisition apparatus according to a first aspect includes a biopsy apparatus; an imaging table that is used to capture an image of a living body disposed on an imaging surface with an imaging apparatus; a projector that projects the image; and at least one processor, in which the processor performs control of projecting relevant information associated with each execution stage of a biopsy that is performed on the living body using the biopsy apparatus, from the projector toward the imaging surface of the imaging table for each execution stage.

In a medical image acquisition apparatus according to a second aspect, in the medical image acquisition apparatus according to the first aspect, in a case where the execution stage of the biopsy is an arrangement stage in which the living body is disposed on the imaging surface of the imaging table, the processor performs control of projecting the disposing position of the living body on the imaging surface of the imaging table and a collection position where a biological tissue is collected from the living body, from the projector toward the imaging surface of the imaging table.

In a medical image acquisition apparatus according to a third aspect, in the medical image acquisition apparatus according to the second aspect, on the basis of a difference in spreading manners of the living body on the imaging surface of the imaging table due to a difference between a type and a compression force of a first compression plate, which is a plate used in a case of capturing an examination image of the living body using the imaging apparatus before the biopsy in order to check the collection position and compresses the living body against the imaging surface of the imaging table, and a type and a compression force of a second compression plate, which is a plate used for the biopsy, has an opening portion on a surface facing the imaging surface of the imaging table, and compresses the living body against the imaging surface of the imaging table, the processor performs control of projecting a disposing position of the living body which is adjusted such that the collection position comes to a center of the opening portion of the second compression plate, from the projector toward the imaging surface of the imaging table.

In a medical image acquisition apparatus according to a fourth aspect, in the medical image acquisition apparatus according to the third aspect, in a case where the living body is disposed at the disposing position of the living body which is adjusted such that the collection position comes to the center of the opening portion of the second compression plate and a contour portion of the living body enters the opening portion of the second compression plate, the processor performs control of projecting the disposing position of the living body which is adjusted such that the contour portion of the living body does not enter the opening portion and the collection position is within a range of the opening portion of the second compression plate, from the projector toward the imaging surface of the imaging table.

In a medical image acquisition apparatus according to a fifth aspect, in the medical image acquisition apparatus according to the third aspect, in a case where there are a plurality of collection positions, the processor performs control of projecting the disposing position of the living body which is adjusted such that each of the collection positions is within a range of the opening portion of the second compression plate, from the projector toward the imaging surface of the imaging table.

In a medical image acquisition apparatus according to a sixth aspect, in the medical image acquisition apparatus according to the first aspect, in a case where the execution stage of the biopsy is a pre-treatment stage where anesthesia is performed on the living body, the processor performs control of further projecting information regarding a position where an anesthetic needle is inserted and a depth to which the anesthetic needle is inserted along a direction intersecting the imaging surface of the imaging table, from the projector toward the imaging surface of the imaging table.

In a medical image acquisition apparatus according to a seventh aspect, in the medical image acquisition apparatus according to the first aspect, in a case where the execution stage of the biopsy is a puncturing stage in which the living body is punctured with a biopsy needle attached to the biopsy apparatus along the imaging surface of the imaging table, the processor performs control of projecting a position of the biopsy needle, a collection position where a biological tissue is collected from the living body, and a distance from a distal end of the biopsy needle to the collection position, from the projector toward the imaging surface of the imaging table.

In a medical image acquisition apparatus according to an eighth aspect, in the medical image acquisition apparatus according to the seventh aspect, the processor performs control of projecting the position of the biopsy needle in accordance with a motion of the biopsy needle, from the projector toward the imaging surface of the imaging table.

In a medical image acquisition apparatus according to a ninth aspect, in the medical image acquisition apparatus according to the first aspect, the execution stage of the biopsy is a needle removal stage in which the biopsy needle inserted to the living body is pulled out from the living body, the processor performs control of projecting an elapsed time from the pulling out of the biopsy needle from the living body, from the projector toward the imaging surface of the imaging table.

In a medical image acquisition apparatus according to a tenth aspect, in the medical image acquisition apparatus according to the ninth aspect, the processor performs control of projecting an elapsed time from a distal end of the biopsy needle that has punctured the living body, being separated from a collection position where a biological tissue of the living body is collected, by a predetermined distance, from the projector toward the imaging surface of the imaging table.

In a medical image acquisition apparatus according to an eleventh aspect, in the medical image acquisition apparatus according to the ninth aspect, the processor performs control of projecting an elapsed time from a distal end of the biopsy needle that has punctured the living body, appearing on an outside of the living body, from the projector toward the imaging surface of the imaging table.

In a medical image acquisition apparatus according to a twelfth aspect, in the medical image acquisition apparatus according to any one of the first to eleventh aspects, the imaging apparatus is a radiography apparatus that captures a radiation image of the living body by irradiating the living body with radiation, and the living body is a breast.

A control program according to a thirteenth aspect is a program executed in a medical image acquisition apparatus including a biopsy apparatus, an imaging table that is used to capture an image of a living body disposed on an imaging surface with an imaging apparatus, a projector that projects the image, and at least one processor, the control program for causing a computer to execute processing of performing control of projecting relevant information associated with each execution stage of a biopsy that is performed on the living body using the biopsy apparatus, from the projector toward the imaging surface of the imaging table for each execution stage.

According to the present disclosure, it is possible to improve an execution accuracy of a biopsy as compared with a case where relevant information associated with a technique regarding the biopsy is provided to the medical worker who performs the biopsy, regardless of the execution stage of the biopsy.

DETAILED DESCRIPTION

Figure 1:
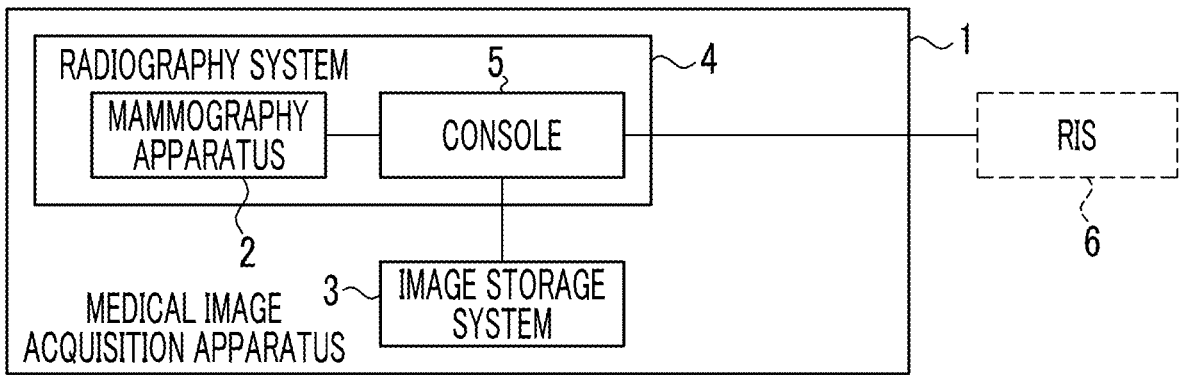
FIG. 1 is a diagram illustrating a configuration example of a medical image acquisition apparatus.

Hereinafter, exemplary embodiments of the present invention will be described in detail with reference to the drawings. The identical components and the identical processing are denoted by the identical reference numerals throughout the drawings, and redundant description will be omitted. Dimensional ratios in the drawings are exaggerated for convenience of description and may be different from the actual ratios.

FIG. 1 is a diagram illustrating a configuration example of a medical image acquisition apparatus 1. The medical image acquisition apparatus 1 is an apparatus that acquires an image used in medical care or examination. The type of the image acquired by the medical image acquisition apparatus 1 is not limited, and may be any image such as a radiation image, an ultrasound image, or a magnetic resonance image (MRI). Hereinafter, the medical image acquisition apparatus 1 will be described using an example in which the medical image acquisition apparatus 1 acquires a radiation image.

The medical image acquisition apparatus 1 includes, for example, an image storage system 3 and a radiography system 4.

The radiography system 4 is a system that images an inside of a body of a subject using radiation. For example, the radiography system 4 includes a mammography apparatus 2 and a console 5. That is, the radiography system 4 captures a radiation image of a breast by the mammography apparatus 2 that is an example of a radiography apparatus. Note that a site of the subject imaged by the radiography system 4 is not limited to the breast, and may be, for example, another site such as the chest or the abdomen. In this case, the mammography apparatus 2 is replaced with a chest X-ray apparatus, a computed tomography (CT) apparatus, or the like.

Note that, in a case where the type of the image acquired by the medical image acquisition apparatus 1 is an ultrasound image, the radiography system 4 is an ultrasound image capturing system, and the mammography apparatus 2 is replaced with an ultrasound image capturing apparatus. In addition, in a case in which the type of the image acquired by the medical image acquisition apparatus 1 is a magnetic resonance image, the radiography system 4 is an MRI imaging system, and the mammography apparatus 2 is replaced with an MRI apparatus. As described above, the mammography apparatus 2, the ultrasound image capturing apparatus, and the MRI apparatus that capture images are examples of an imaging apparatus.

The console 5 is an operation console that is used to operate the mammography apparatus 2 and is connected to, for example, the mammography apparatus 2 and the image storage system 3.

The image storage system 3 is, for example, a system that stores radiation images captured by the radiography system 4. The image storage system 3 extracts a radiation image corresponding to a request from the console 5, from the stored radiation images, and transmits the extracted radiation image to the console 5. A specific example of the image storage system 3 is picture archiving and communication systems (PACS), for example.

The console 5 has a function of controlling the mammography apparatus 2 by using an imaging order and various kinds of information acquired from a radiology information system (RIS) 6 via a communication line such as a LAN, an instruction received from the medical worker, and the like.

Figure 2:
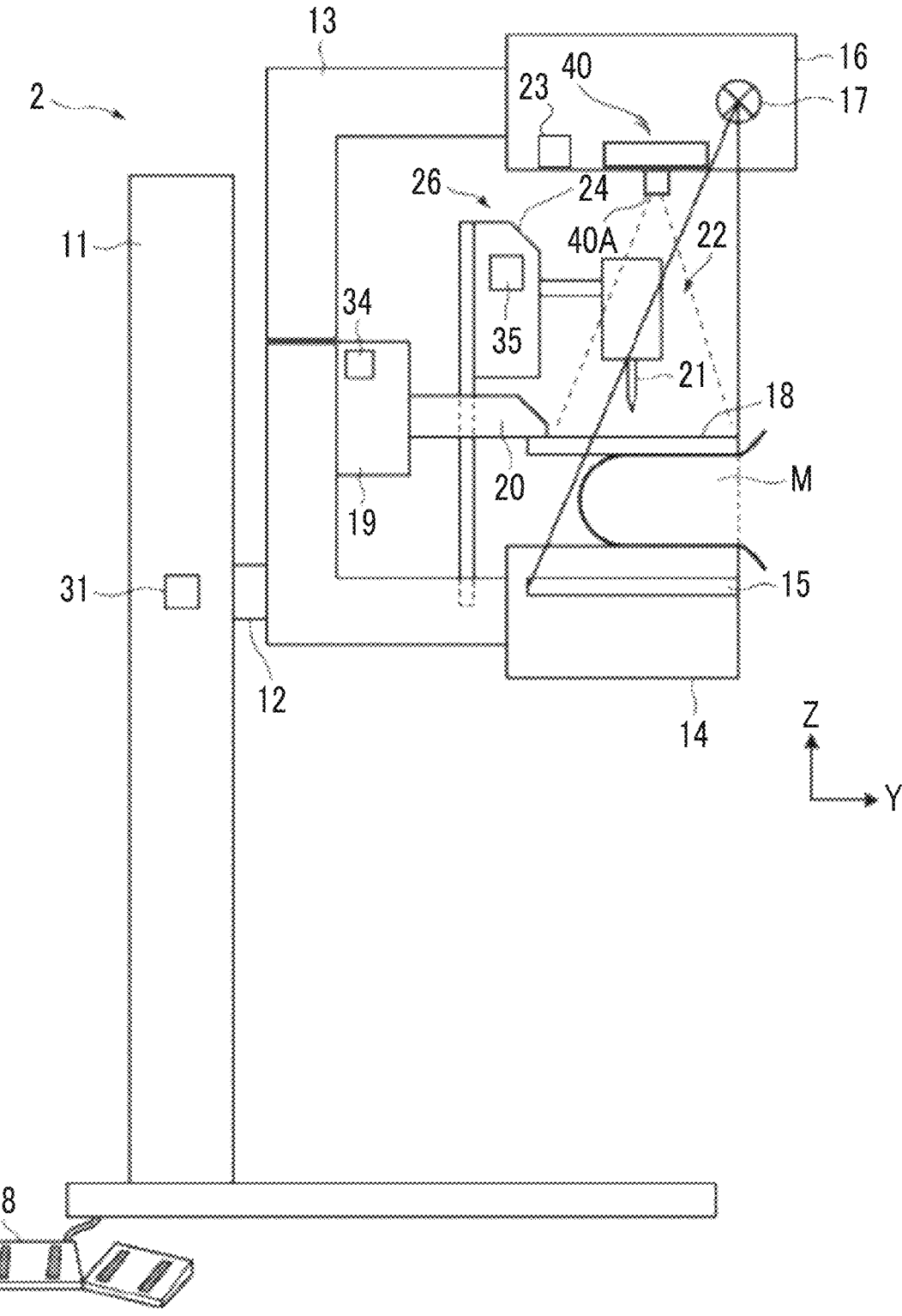
FIG. 2 is a schematic configuration diagram illustrating an example of a mammography apparatus.

FIG. 2 is a schematic configuration diagram illustrating an example of the mammography apparatus 2 according to the present embodiment.

As illustrated in FIG. 2, in the mammography apparatus 2 according to the present embodiment, for example, a radiation accommodation portion 16 that accommodates a radiation irradiator 17 therein and an imaging table 14 are connected to an arm 13 so as to face each other. The breast of the subject is disposed on an upper surface (hereinafter, referred to as an "imaging surface") of the imaging table 14, and the radiation irradiator 17 irradiates the breast with radiation in response to the instruction from the console 5.

Inside the imaging table 14, an image recording medium such as a radiation detector 15 is set in a state of being accommodated in a recording medium holding portion such as a cassette, and a radiation image of the breast is obtained by the radiation detector 15 detecting the radiation that has passed through the breast, which is a test object.

Note that an imaging surface or the like in contact with the breast of the subject is formed of carbon or the like from the viewpoint of the transmittance and the intensity of the radiation.

The arm 13 is attached to a base 11 with a C-axis 12. In addition, the arm 13 is attached to the base 11 by attaching the C-axis 12, which is the center of rotation, to a center position of the radiation detector 15 such that the center of rotation of the arm 13 is the center of the radiation detector 15 in an X direction (refer to FIG. 3).

The base 11 is provided with an operating part 28 that receives an irradiation instruction of the radiation for the radiation irradiator 17 and that is used by the medical worker to adjust a height of the imaging table 14 (that is, a height of the arm 13) and an inclination of the imaging table 14 (that is, an inclination of the arm 13), and an arm controller 31 that moves the arm 13 up and down and rotates the arm 13 in accordance with an input from the operating part 28.

The arm controller 31 adjusts the inclination of the arm 13 by rotating the C-axis 12 attached to the base 11, and adjusts the height of the imaging table 14 by moving the arm 13 up and down.

At a center portion of the arm 13, a compression plate 18 that is a plate disposed above the imaging table 14 and that holds and compresses the breast, a support portion 20 that supports the compression plate 18, and a compression plate moving mechanism 19 that moves the support portion 20 in an up-down direction along the arm 13 are provided. The position and the compression force of the compression plate 18 are controlled by a compression plate controller 34 provided in the compression plate moving mechanism 19. The compression plate 18 is formed of a material having excellent radiation transmittance. Examples of the material for the compression plate 18 include resins such as polymethylpentene, polycarbonate, acrylic, and polyethylene terephthalate. Note that the member constituting the compression plate 18 is not limited to the above-mentioned example. For example, the member constituting the compression plate 18 may be a film-shaped member.

Figure 3:
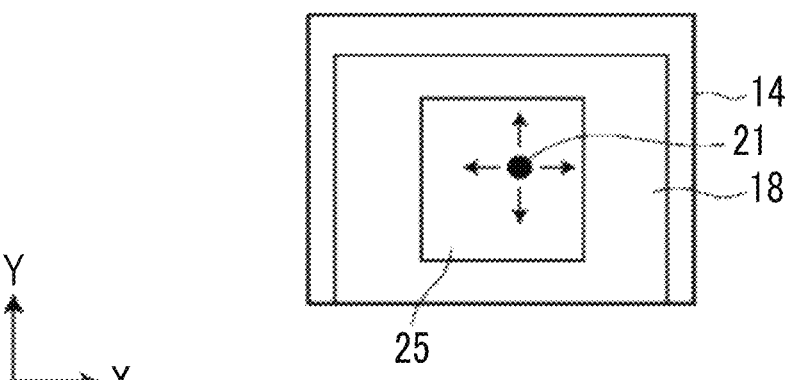
FIG. 3 is a diagram illustrating an example of a case where a compression plate is viewed from above.

FIG. 3 is a diagram illustrating the compression plate 18 as viewed from above, that is, a diagram illustrating the compression plate 18 as viewed from the radiation accommodation portion 16 toward the imaging table 14 along a Z direction. As illustrated in FIG. 3, the compression plate 18 includes an opening portion 25 such that a biopsy can be performed in a state where the breast is fixed by the imaging table 14 and the compression plate 18.

As an example, a biopsy unit 26 as a biopsy apparatus of the present disclosure illustrated in FIG. 2 includes a biopsy needle 21 that punctures the breast, and a biopsy needle unit 22, and further includes a moving mechanism 24 that moves the biopsy needle unit 22 in X, Y, and Z directions. The position of a distal end of the biopsy needle 21 of the biopsy needle unit 22 is controlled by a needle position controller 35 of the moving mechanism 24. Note that in FIG. 2, a horizontal direction is the Y direction, a vertical direction is the Z direction, and a direction perpendicular to a YZ plane is the X direction. The Z direction is also a vertical direction.

The biopsy unit 26 punctures a site as a biopsy target, that is, a collection position (hereinafter, referred to as a "target T") at which the biological tissue is collected, with the hollow biopsy needle 21, and cuts the biological tissue of the target T by an inner blade provided in the biopsy needle 21 by using a force of a spring. Note that the biopsy unit 26 may acquire the biological tissue of the target T by suctioning through a hollow portion of the biopsy needle 21.

The biopsy unit 26 illustrated in FIG. 2 shows an example in which a so-called vertical direction puncture is performed in which the biopsy needle 21 is moved in the Z direction to perform a puncture from above the breast, but the biopsy unit 26 also copes with a puncture in a lateral direction. The puncture in the lateral direction is a method of moving the biopsy needle 21 in the X direction of FIG. 3 and puncturing the breast from the side surface. Whether to perform the puncture in the vertical direction or to perform the puncture in the lateral direction is decided by the medical worker in consideration of the case of collecting the biological tissue based on the position of the target T.

In a case where the puncture is performed in the lateral direction, for example, a lateral adapter 27 is attached to the biopsy needle unit 22, and the biopsy needle 21 is attached to the lateral adapter 27.

Figure 4:
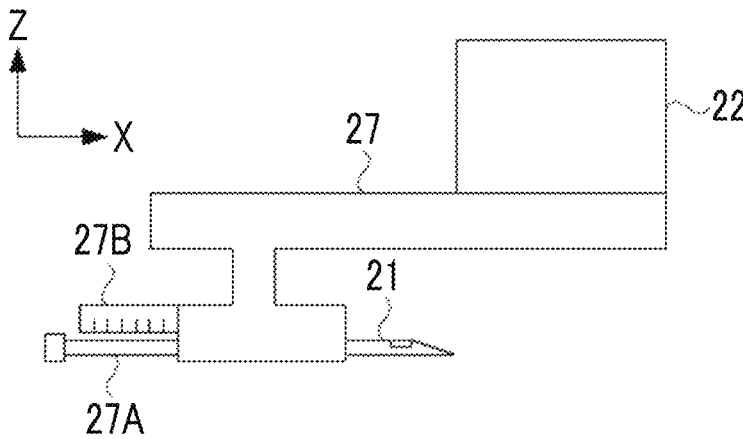
FIG. 4 is a diagram illustrating an example of a lateral adapter.

FIG. 4 is a diagram illustrating an example of the lateral adapter 27 attached to the biopsy needle unit 22. In the lateral adapter 27, the medical worker operates a position adjustment mechanism (not illustrated) of the lateral adapter 27 to adjust the position of the distal end of the biopsy needle 21 in the YZ plane. The biopsy needle 21 attached to the lateral adapter 27 is moved in the X direction in conjunction with, for example, the movement of a handle 27A operated by the medical worker along the X direction.

That is, in a case of the puncture using the lateral adapter 27, the position of the distal end of the biopsy needle 21 is not controlled by the needle position controller 35, but is decided by the operation of the medical worker. After the medical worker decides the position of the biopsy needle 21 in the Y direction and the Z direction in consideration of the position of the target T, the medical worker moves the handle 27A toward the breast along the X direction while checking, for example, graduations 27B, and pierces the breast with the biopsy needle 21 from the side surface of the breast to the position of the target T.

The lateral adapter 27 includes a displacement sensor (not illustrated) that measures a movement amount of the biopsy needle 21 along the X direction, and a measurement value of the displacement sensor is notified to, for example, the needle position controller 35. That is, in a case of the puncture using the lateral adapter 27, the biopsy unit 26 cannot adjust the position of the distal end of the biopsy needle 21 by the needle position controller 35, but can acquire the position of the distal end of the biopsy needle 21 in the X direction.

The lateral adapter 27 illustrated in FIG. 4 is attached to move the biopsy needle 21 from the left to the right, but the lateral adapter 27 can move the biopsy needle 21 from the right to the left by changing the attachment direction of the lateral adapter 27.

On the other hand, as illustrated in FIG. 2, a projector 40 in which a projection unit 40A is provided on a lower surface of the radiation accommodation portion 16 and in the vicinity of an emission port of the radiation emitted by the radiation irradiator 17 is built in the radiation accommodation portion 16. The projector 40 projects an image (hereinafter, referred to as a "projection image") indicating various kinds of information to the imaging surface. Therefore, in a case where the breast is disposed on the imaging surface, the projection image is projected onto the breast. In addition, in a case where the compression plate 18 compresses the breast, the projection image is also projected onto the compression plate 18. Note that, since the opening portion 25 is present in the compression plate 18, in this case, the projection image is projected onto the compression plate 18, the breast not covered with the compression plate 18, and the imaging surface in a range where the breast is not disposed.

As the projector 40, known projectors such as a liquid crystal projector, a Digital Light Processing (DLP) (registered trademark) projector, and a laser projector can be used.

As described above, the mammography apparatus 2 is provided with the biopsy unit 26, and the arm 13 having one end part side provided with the projector 40 and the radiation irradiator 17 that emits radiation for capturing radiation images toward the imaging surface of the imaging table 14 and having the other end part side provided with the imaging table 14.

Note that, in the mammography apparatus 2, before performing the puncture, for example, a scout image obtained by imaging the breast to be biopsied from two directions to include a region as the target T is acquired. The scout image is a radiation image viewed from different viewpoints to check the position of the target T. The distance from the bottom surface (the side that presses the breast) of the compression plate 18 to the target T and the position on the XY plane can be obtained from the deviation of the target T in the two scout images, and thus three-dimensional positional information of the target T can be obtained.

The method of acquiring the three-dimensional positional information of the target T in the breast is not limited to the method using the scout images. The mammography apparatus 2 can perform stereo imaging. In the stereo imaging, radiation is emitted by the radiation irradiator 17 from each of two irradiation positions having different irradiation angles toward the breast, and two radiation images of the breast are captured. That is, in the stereo imaging, the imaging is performed while the angles of the imaging table 14, the compression plate 18, the breast, and the like are fixed and the rotation angle of the radiation irradiator 17 with respect to the base 11 is changed.

Further, the mammography apparatus 2 can perform tomosynthesis imaging. In the tomosynthesis imaging, radiation is emitted by the radiation irradiator 17 from each of a plurality of irradiation positions having different irradiation angles toward the breast, and a plurality of radiation images of the breast are captured. That is, even in the tomosynthesis imaging, the imaging is performed while the angles of the imaging table 14, the compression plate 18, the breast, and the like are fixed and the rotation angle of the radiation irradiator 17 with respect to the base 11 is changed.

Figure 5:
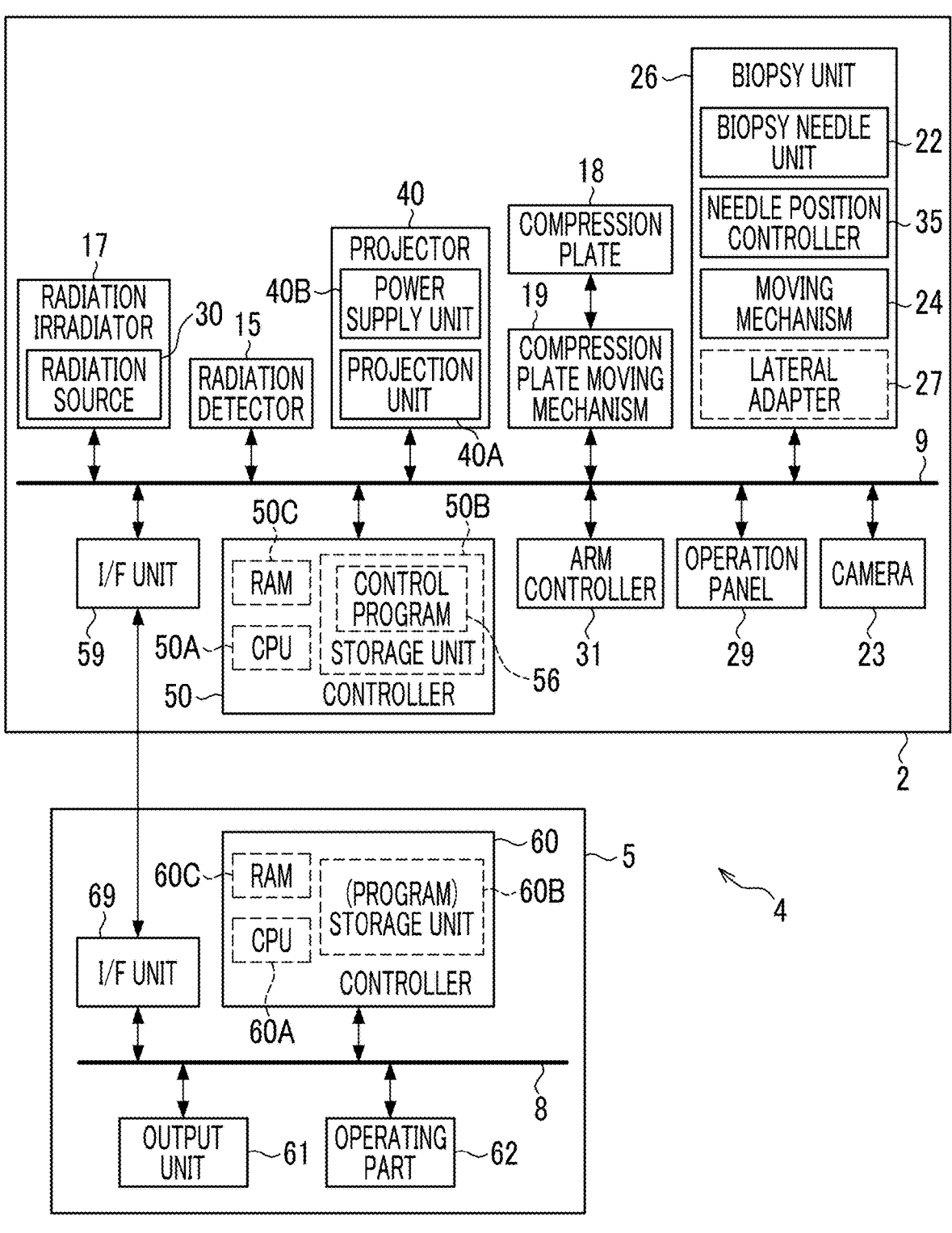
FIG. 5 is a diagram illustrating a configuration example of the mammography apparatus and a console.

Next, a configuration example of the radiography system 4 will be described. FIG. 5 is a diagram illustrating a configuration example of the mammography apparatus 2 and the console 5 included in the radiography system 4.

The mammography apparatus 2 is configured by a computer as an example. As illustrated in FIG. 5, the mammography apparatus 2 includes the radiation detector 15, the radiation irradiator 17, the compression plate 18, the compression plate moving mechanism 19, a camera 23, the biopsy unit 26, an operation panel 29, the arm controller 31, the projector 40, a controller 50, and an interface (I/F) unit 59. The radiation detector 15, the radiation irradiator 17, the compression plate moving mechanism 19, the camera 23, the biopsy unit 26, the operation panel 29, the arm controller 31, the projector 40, the controller 50, and the I/F unit 59 are connected to each other via a bus 9 such that various kinds of information can be exchanged.

The controller 50 controls the operation of the mammography apparatus 2 on the basis of an instruction from the medical worker. The controller 50 includes a central processing unit (CPU) 50A as an example of a processor, a storage unit 50B, and a random access memory (RAM) 50C. The storage unit 50B stores, in advance, various programs including a control program 56 that the CPU 50A reads in order to perform the control related to the capturing of the radiation image and the control related to the biopsy, and various parameters that the CPU 50A refers to in a case of controlling the operation of the mammography apparatus 2. The RAM 50C is used as a temporary work area of the CPU 50A.

The operation panel 29 has a function of setting various kinds of instructional information such as exposure conditions and posture information, various operation instructions such as the rotation angle of the arm 13, and the like by the medical worker. For example, the exposure condition set by the operation panel 29 includes information such as a tube voltage, a tube current, and an irradiation time. Note that the operation panel 29 is provided with a display that displays a response from the mammography apparatus 2 to the setting of the medical worker or various kinds of information.

In a case where the controller 50 receives an instruction from the medical worker through the operation panel 29 or the console 5, the controller 50 controls the operation of each unit constituting the mammography apparatus 2 in accordance with the instructed content. For example, in a case where the controller 50 receives the irradiation instruction of the radiation from the medical worker, the controller 50 controls the radiation irradiator 17 such that a radiation source 30 provided in the radiation irradiator 17 irradiates the imaging surface of the imaging table 14 with the radiation in accordance with the designated exposure conditions.

The radiation detector 15 detects the radiation that has passed through the breast as the test object, in response to the instruction from the controller 50. The radiation detector 15 is disposed inside the imaging table 14. In the mammography apparatus 2, in a case of capturing the radiation image, the breast of the subject is disposed on the imaging surface of the imaging table 14. A loading surface or the like in contact with the breast of the subject is formed of, for example, carbon from the viewpoint of the transmittance and the intensity of the radiation.

The compression plate moving mechanism 19 moves the compression plate 18 up and down along the Z direction in accordance with the instruction of the controller 50 that has received the operation content of the medical worker, performed through the compression plate controller 34 to perform the compression and the compression release of the breast by the compression plate 18.

The arm controller 31 controls the rotation angle of the C-axis 12 such that the rotation angle of the arm 13 is an angle corresponding to imaging, in accordance with the instruction of the controller 50.

The biopsy unit 26 collects the biological tissue of the target T in the breast by the moving mechanism 24 moving the biopsy needle 21 in response to the instruction of the needle position controller 35 controlled by the controller 50. In addition, the biopsy unit 26 notifies the controller 50 of the positional information of the distal end of the biopsy needle 21 through the needle position controller 35. Note that, as already described, in a case where the lateral adapter 27 is attached to the biopsy needle unit 22 of the biopsy unit 26 and the puncture is performed in the lateral direction, the movement of the biopsy needle 21 is performed by the operation of the handle 27A by the medical worker.

The camera 23 is attached at a position to face the imaging surface of the imaging table 14 such that the entire breast disposed on the imaging surface of the imaging table 14 is included within an angle of view, and images a state of the breast disposed on the imaging surface of the imaging table 14 and a procedure of the medical worker with respect to the breast in accordance with the instruction of the controller 50. The image captured by the camera 23 may be a visible image or an infrared image, and may be a still image or a motion picture. Hereinafter, as an example, it is assumed that the camera 23 captures a visible image. Note that the camera 23 illustrated in FIG. 2 is attached to the radiation accommodation portion 16, but this is an example. There is no restriction on the attachment position of the camera 23 as long as the entire breast can be imaged along the Z direction, and the camera 23 may be attached to, for example, the arm 13 or the biopsy unit 26.

The projector 40 includes the projection unit 40A and a power supply unit 40B. Turning on and off of the power supply unit 40B is controlled in accordance with the instruction from the controller 50, and the projector 40 projects the projection image including information regarding the biopsy notified from the controller 50, from the projection unit 40A toward the imaging surface of the imaging table.

The I/F unit 59 performs communication for various kinds of information with an external apparatus connected to a communication line such as a LAN, by using wireless communication or wired communication. For example, the controller 50 transmits the captured radiation image and visible image of the breast to the console 5 via the I/F unit 59.

The console 5 is configured by using a computer as an example. As illustrated in FIG. 5, the console 5 includes a controller 60, an output unit 61, an operating part 62, and an I/F unit 69. The controller 60, the output unit 61, the operating part 62, and the I/F unit 69 are connected to each other via a bus 8 such that various kinds of information can be exchanged.

The controller 60 controls the overall operation of the console 5. The controller 60 includes a CPU 60A, a storage unit 60B, and a RAM 60C. Various programs and the like executed by the CPU 60A are stored in the storage unit 60B in advance. In addition, the storage unit 60B stores the radiation image and the visible image captured by the mammography apparatus 2, various kinds of other information, and the like. The storage unit 60B is an example of a storage device that maintains the stored information even in a case where power to be supplied to the storage unit 60B is cut off. For example, a semiconductor memory such as an SSD is used, or a hard disk may be used. The RAM 60C is used as a temporary work area of the CPU 60A.

The output unit 61 outputs information processed by the controller 60 to the medical worker.

The operating part 62 is used for the medical worker to input instructions related to the capturing of the radiation image including the irradiation instruction of the radiation, various kinds of information such as exposure conditions and posture information, and the like. Therefore, the operating part 62 includes an irradiation instruction button that is pressed by the medical worker in a case of instructing the irradiation of the radiation, for example. An operation form of the operating part 62 is not limited, and, for example, an operation by a switch, a touch panel, a touch pen, a mouse, or the like can be received.

The I/F unit 69 performs communication for various kinds of information with the mammography apparatus 2, the RIS 6, and the image storage system 3 that are connected to, for example, a communication line such as LAN, by using wireless communication or wired communication. For example, the console 5 receives the radiation image and the visible image captured by the mammography apparatus 2 via the I/F unit 69, transmits the received radiation image and visible image to the image storage system 3 via the I/F unit 69, and stores the radiation image and the visible image in the image storage system 3.

Figure 6:
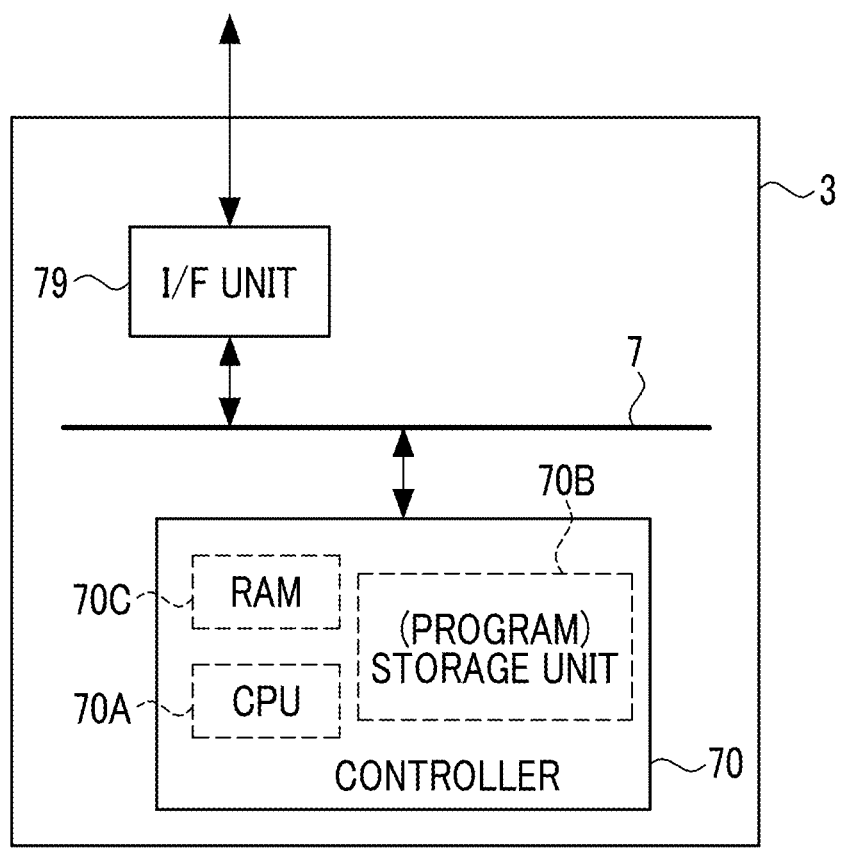
FIG. 6 is a diagram illustrating a configuration example of an image storage system.

On the other hand, FIG. 6 is a diagram illustrating a configuration example of the image storage system 3. As illustrated in FIG. 6, the image storage system 3 includes a controller 70 and an I/F unit 79. The controller 70 and the I/F unit 79 are connected to each other via a bus 7 such that various kinds of information can be exchanged.

The controller 70 controls an operation of the image storage system 3. The controller 70 includes a CPU 70A, a storage unit 70B, and a RAM 70C. The storage unit 70B stores, in advance, various programs that are read by the CPU 70A in order to perform control related to the storage of the radiation image and the visible image, and various parameters to be referred to by the CPU 70A in a case of controlling the operation of the image storage system 3. In addition, the storage unit 70B stores the radiation image and the visible image in association with the imaging order, the information regarding the subject, and the like. That is, the storage unit 70B functions as a database of the image. The RAM 70C is used as a temporary work area of the CPU 70A.

The I/F unit 79 performs communication for various kinds of information with an external apparatus connected to a communication line such as a LAN, by using wireless communication or wired communication. For example, the controller 70 transmits the radiation image requested through the console 5 to the console 5 via the I/F unit 79.

Next, the operation of the mammography apparatus 2 in a case where the medical worker performs a biopsy on a breast will be described in detail.

Figure 7:
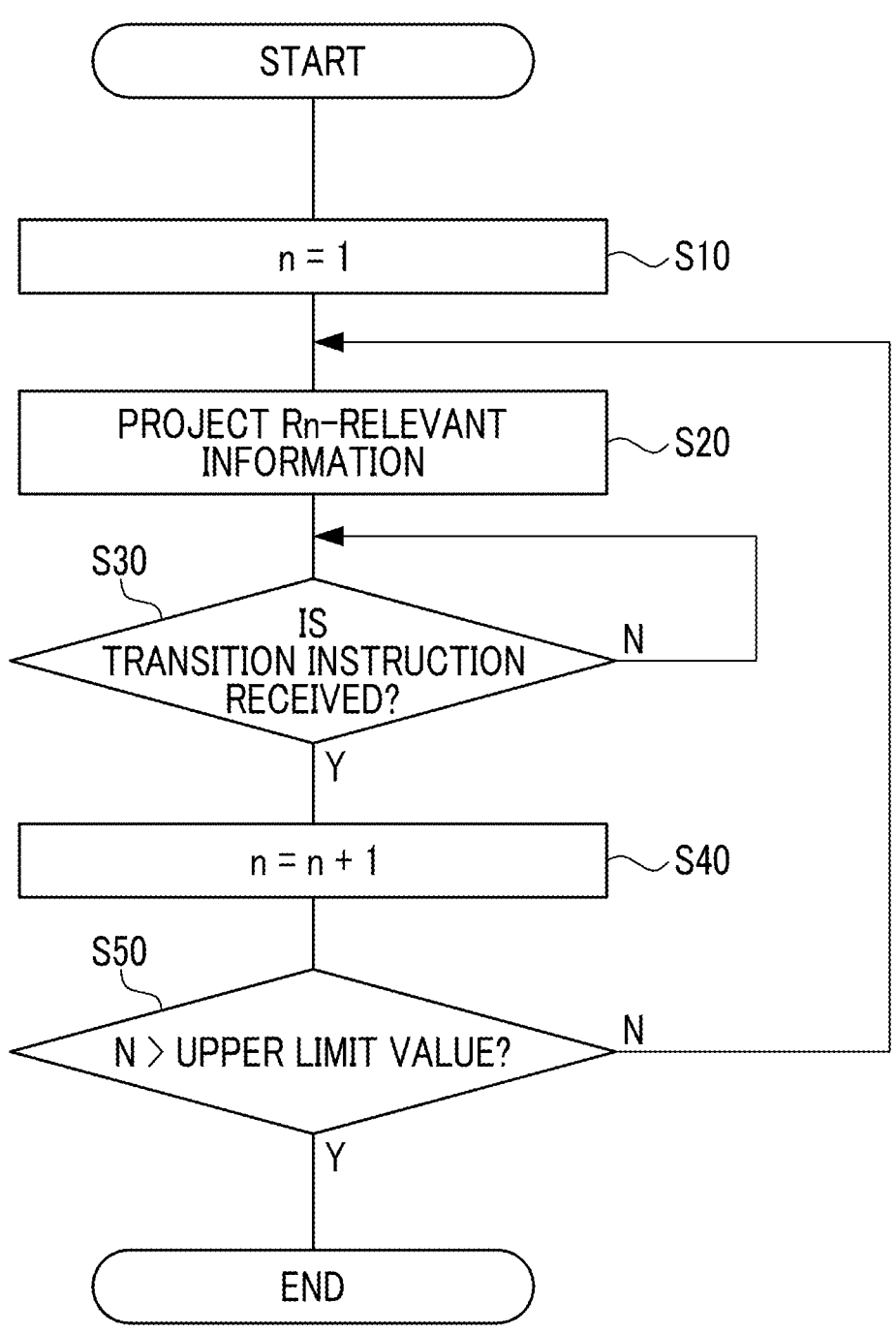
FIG. 7 is a flowchart illustrating an example of a flow of biopsy support processing.

FIG. 7 is a flowchart illustrating an example of a flow of biopsy support processing for the medical worker, executed by the mammography apparatus 2 in a case where a start instruction of the biopsy is received. The CPU 50A of the mammography apparatus 2 reads the control program 56 from the storage unit 50B to execute the biopsy support processing.

Here, as an example, a case will be described in which the lateral adapter 27 is attached to the biopsy needle unit 22 of the biopsy unit 26 and the biopsy needle 21 performs the puncture in the lateral direction.

Note that, before the execution of the biopsy, the mammography apparatus 2 captures a radiation image of the breast to be used as an examination image, and the position of the target T in the breast is specified in advance by diagnosing the radiation image. For example, the medical worker may select a radiation image that is close to the angle of the arm 13 in a case where the biopsy is performed, from the radiation images captured at various irradiation angles, and specify the position of the target T from the selected radiation image. In addition, the position of the target T may be specified from the radiation image by using computer aided diagnosis (CAD). The position of the target T is represented by, for example, a coordinate value in three-dimensional coordinates virtually set on the imaging surface of the imaging table 14. The specified position of the target T is input from, for example, the console 5 or the operation panel 29 by the medical worker, and is stored in the storage unit 50B of the controller 50.

For example, in a case where a registration operation for subject information from the console 5 by the medical worker is performed with the start instruction of the biopsy as a trigger, in step S10, the controller 50 sets an index n stored in the RAM 50C to "1". The index n is an identifier indicating an execution stage R of the biopsy.

The biopsy is divided into each execution stage R of "positioning", "anesthesia", "biopsy needle position adjustment", "biopsy needle puncture", and "biopsy needle removal", and is executed in the order of "positioning", "anesthesia", "biopsy needle position adjustment", "biopsy needle puncture", and "biopsy needle removal".

The positioning is a step of adjusting the position of the breast of the subject such that the biological tissue of the target T can be collected by the biopsy needle 21. That is, the positioning is an arrangement stage of arranging the living body on the imaging surface of the imaging table 14.

The anesthesia is a step of injecting an anesthetic solution into the breast by performing puncture on the breast with the anesthetic needle (not illustrated) in advance before performing the puncture on the breast with the biopsy needle 21 in order to alleviate the pain caused in a case where the biological tissue is collected from the target T by the biopsy needle 21.

The biopsy needle position adjustment is a step of adjusting the position of the distal end of the biopsy needle 21 before puncturing the breast with the biopsy needle 21 such that the distal end of the biopsy needle 21 reaches the target T.

The biopsy needle puncture is a step of moving the distal end of the biopsy needle 21 to the position of the target T to collect the biological tissue of the target T.

The biopsy needle removal is a step of pulling out the biopsy needle 21 from the breast after the collection of the biological tissue of the target T.

The index n indicates the execution stage R of the biopsy that is being performed by the medical worker according to the value of n. For example, the index n=1 corresponds to an execution stage R1 of positioning, the index n=2 corresponds to an execution stage R2 of anesthesia, the index n=3 corresponds to an execution stage R3 of the biopsy needle position adjustment, the index n=4 corresponds to an execution stage R4 of the biopsy needle puncture, and the index n=5 corresponds to an execution stage R5 of biopsy needle removal. For convenience of the description, in a case of describing the steps of the respective execution stages R separately, the execution stage R may be expressed as "execution stage Rn" (n=1 to 5). The upper limit value of the index n, that is, the number of steps (in this case, "5") included in the execution stage R of the biopsy is stored in advance in, for example, the storage unit 50B.

The classification of the execution stage R of the biopsy according to the present disclosure is an example, and classifications different from the above example may be performed. In this case, the value of the index n may be associated with each step in ascending order according to the order of the execution stages R of the biopsy. In addition, the trigger for starting the biopsy is not limited to the registration operation of the subject information, and may be, for example, an operation of the compression plate controller 34.

In step S20, the controller 50 performs control of projecting the relevant information associated with each of the execution stages Rn, from the projector 40 toward the imaging surface of the imaging table 14.

The relevant information associated with each of the execution stages Rn is information that is preferably referred to by the medical worker in a case of performing the technique in the execution stages Rn of the biopsy. In the following, the relevant information associated with each of the execution stages Rn will be referred to as "Rn-relevant information". The Rn-relevant information includes only the information used in the execution stages Rn of the biopsy.

In a case where the index n is set to "1", the controller 50 performs control of projecting the R1-relevant information from the projector 40 toward the imaging surface of the imaging table 14.

Specifically, the controller 50 controls the projection unit 40A of the projector 40 to project the position of the target T and the disposing position of the breast toward the imaging surface of the imaging table 14. The disposing position of the breast is represented by a skin line 32 representing a contour of the breast displayed on the imaging surface of the imaging table 14.

Figure 8:
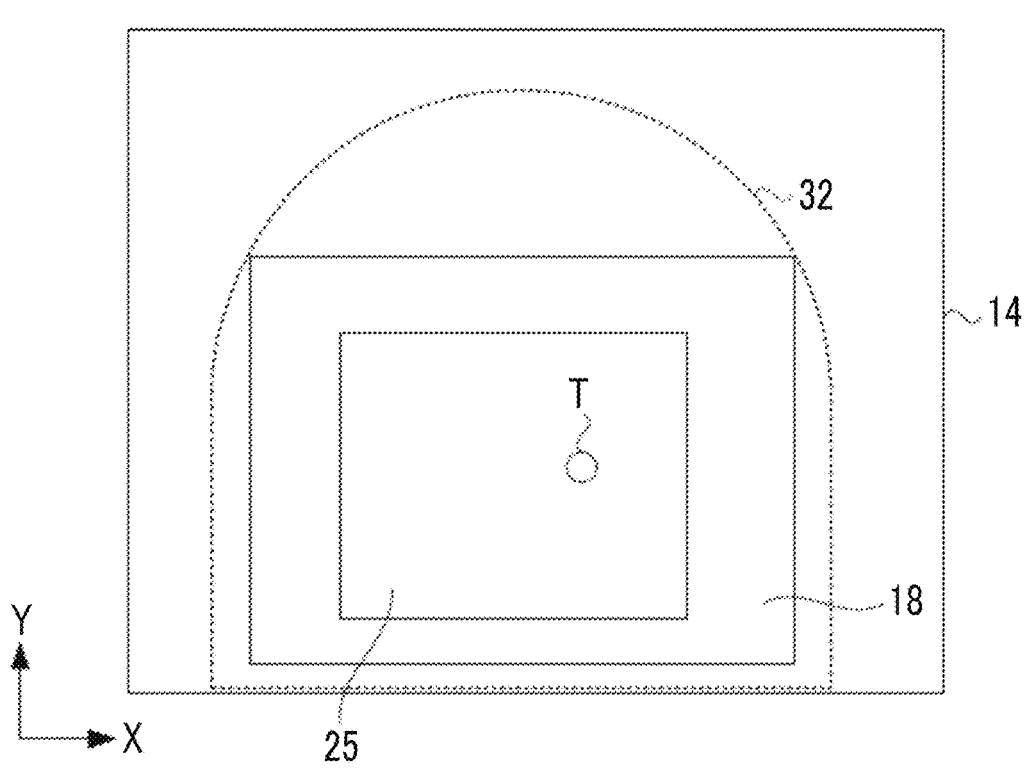
FIG. 8 is a diagram illustrating an example of R1-relevant information projected in an execution stage R1.

FIG. 8 is a diagram illustrating an example of the position of the target T and the skin line 32 projected onto the imaging surface of the imaging table 14.

The controller 50 calculates the position of the skin line 32 such that the target T is within a range of the opening portion 25 of the compression plate 18, from the positional information of the opening portion 25 obtained from the type of the compression plate 18 attached to the mammography apparatus 2, the position of the target T specified from the radiation image, and the position of the breast in a case where the radiation image is captured. The controller 50 performs control of projecting the skin line 32 to the calculated position.

Therefore, as compared with a case where a subject is requested to dispose the breast on the imaging surface of the imaging table 14 and then whether or not the target T is within the range of the opening portion 25 of the compression plate 18 at that position is checked, it is not necessary for the subject to repeatedly change the position of the breast, and the burden on the subject is reduced.

Note that the position of the target T is information specified from the examination image, but in a case of capturing the examination image, a different type of compression plate (hereinafter, referred to as an "imaging compression plate") from the compression plate 18 that is used for the biopsy is used. In addition, the compression force on the breast by the compression plate 18 used for the biopsy and the compression force on the breast by the imaging compression plate are different in some cases.

In addition, a spreading manner of the breast compressed by the compression plate 18 may be different from a spreading manner of the breast compressed by the imaging compression plate. In a case where the spreading manner of the breast is different, even though the breast is disposed at the calculated position of the skin line 32, the target T may not be within the range of the opening portion 25 of the compression plate 18.

Therefore, even in a case where the breast is compressed with a compression force, which is different from the compression force of the imaging compression plate, by the compression plate 18 being a type different from the imaging compression plate, the controller 50 adjusts the projection position of the skin line 32 on the imaging surface of the imaging table 14 such that the target T comes to the center of the opening portion 25 of the compression plate 18.

Therefore, the storage unit 50B stores a conversion table in advance. The conversion table is a table in which each combination of the type of compression plate 18 and the compression force on the breast by the compression plate 18 is associated with each combination of the type of imaging compression plate and the compression force on the breast by the imaging compression plate, a deviation amount of the target T in a case where the breast is compressed with the corresponding compression force by the corresponding type of compression plate 18 is shown. The deviation amount of the target T is a deviation amount between the position of the target T in a case where the breast is disposed at the disposing position of the breast at the time of capturing the examination image and the position of the target T in a case where the breast is compressed by the compression plate 18 in a state where the breast is disposed at the same position as the disposing position of the breast at the time of capturing the examination image.

In a case where the subject disposes the breast on the imaging surface of the imaging table 14, the controller 50 adjusts the position of the skin line 32 such that the target T comes to the center of the opening portion 25 of the compression plate 18, on the basis of the disposing position of the breast at the time of capturing the examination image, the deviation amount of the target T obtained from the conversion table, which corresponds to the combination of the type of the imaging compression plate and the compression force on the breast used for capturing the examination image and the type of the compression plate 18 and the compression force on the breast used for the biopsy, and the positional information of the opening portion 25 of the compression plate 18 used for the biopsy.

The disposing position of the breast at the time of capturing the examination image and the positional information of the opening portion 25 of the compression plate 18 are stored in advance in, for example, the storage unit 50B.

The type of the compression plate 18 attached to the mammography apparatus 2 may be input in advance from the console 5 or the operation panel 29 by the medical worker, or the type of the compression plate 18 may be acquired by reading a barcode label attached to the compression plate 18 using a barcode reader (not illustrated) provided in the mammography apparatus 2. The barcode reader is provided, for example, at a position where the barcode label can be read in a state in which the compression plate 18 is attached to the support portion 20.

Note that the center of the opening portion 25 of the compression plate 18 is the center of the opening portion 25 of the compression plate 18 in a case where the compression plate 18 is viewed from the radiation accommodation portion 16 toward the imaging table 14 along the Z direction. The center of the opening portion 25 of the compression plate 18 is represented by a predetermined range including the center of the opening portion 25. The fact that the position of the target T is included in the range is referred to as "the target T comes to the center of the opening portion 25 of the compression plate 18". The imaging compression plate is an example of a first compression plate, and the compression plate 18 is an example of a second compression plate.

In a case where the subject disposes the breast along the skin line 32 adjusted such that the target T comes to the center of the opening portion 25 of the compression plate 18, in a case where the breast is compressed by the compression plate 18, the contour portion of the breast may enter the opening portion 25 of the compression plate 18, and thus the breast may not be compressed. In such a case, the controller 50 adjusts the position of the skin line 32 such that the contour portion of the breast does not enter the opening portion 25 of the compression plate 18 and the target T is within the range of the opening portion 25 of the compression plate 18. Moreover, the controller 50 performs control of projecting the projection image including the skin line 32 of which the position is adjusted, from the projector 40 toward the imaging surface of the imaging table 14.

In addition, in a case where a plurality of targets T are present in the breast, the controller 50 performs control of projecting the projection image including the skin line 32 of which the position is adjusted such that all the targets T are within the range of the opening portion 25 of the compression plate 18, from the projector 40 toward the imaging surface of the imaging table 14.

Depending on the position of the target T, not all targets T may necessarily be within the range of the opening portion 25 of the compression plate 18. In such a case, the controller 50 performs control of projecting the projection image including the skin line 32 of which the position is adjusted such that as many high-priority targets T as possible are within the range of the opening portion 25 of the compression plate 18 by referring to the priorities of the targets T, from the projector 40 toward the imaging surface of the imaging table 14.

The priority of the target T is set in advance by the medical worker, and is stored in the storage unit 50B in association with each target T. The medical worker may, for example, set the priority higher as the malignancy degree of the target T is higher, and may, for example, set the priority higher as the size of the target T is larger.

In this case, the controller 50 performs control of projecting the projection image including the skin line 32 of which the position is adjusted such that the remaining targets T, which are not within the range of the opening portion 25 of the compression plate 18, are within the range of the opening portion 25, after the biopsy for the breast disposed along the current skin line 32 is ended, from the projector 40 toward the imaging surface of the imaging table 14. By preferentially causing the target T having a high priority to be within the range of the opening portion 25 of the compression plate 18, the higher the priority, the earlier the biopsy is performed, and the examination results are obtained.

In a case where the subject disposes the breast along the skin line 32 projected onto the imaging surface of the imaging table 14, the medical worker notifies the mammography apparatus 2 of a compression instruction to perform compression on the breast, for example, from the console 5 or the operation panel 29. On the other hand, the controller 50 controls the compression plate moving mechanism 19 to move the compression plate 18 toward the imaging surface of the imaging table 14, and the compression plate 18 compresses the breast disposed on the imaging surface along the skin line 32.

The controller 50 controls the camera 23 to capture the visible image of the breast compressed by the compression plate 18, and in a case where a portion where the position of the contour of the breast in the XY plane deviates from the skin line 32 by a predetermined distance or more is recognized from the visible image, the controller 50 controls the compression plate moving mechanism 19 to release the compression on the breast by the compression plate 18, and the subject is requested to rearrange the breast.

In addition, the controller 50 may control the radiation irradiator 17 to capture the radiation image of the breast compressed by the compression plate 18 in accordance with the instruction of the medical worker. In a case where the position of the target T specified from the captured radiation image and the position of the target T specified in advance by the examination image deviate from each other by a predetermined distance or more, the controller 50 controls the compression plate moving mechanism 19 to release the compression on the breast by the compression plate 18, and the subject is requested to rearrange the breast.

As described above, the skin line 32 and the position of the target T are examples of the R1-relevant information associated with the execution stage R1.

In a case where the execution stage R1 is completed, the medical worker notifies the mammography apparatus 2 of a transition instruction to perform transition to the next execution stage R, from the console 5 or the operation panel 29, for example. Since the next execution stage R is anesthesia, for example, an operation of transmitting coordinate values of the position M where the anesthetic needle is inserted is the transition instruction.

Therefore, in step S30, the controller 50 determines whether or not the transition instruction is received. In a case where the transition instruction is not received, the controller 50 repeatedly executes the determination processing of step S30, and waits until the treatment of the currently executed execution stage R is completed. On the other hand, in a case where the transition instruction is received, the processing proceeds to step S40.

In step S40, the controller 50 updates the index n by adding "1" to the index n. That is, the execution stage R of the biopsy is advanced by one.

In step S50, the controller 50 determines whether or not the index n exceeds the upper limit value. In a case where the index n exceeds the upper limit value, it means that all the execution stages R of the biopsy are ended. Therefore, the controller 50 ends the biopsy support processing illustrated in FIG. 7.

On the other hand, in a case where the index n is equal to or lower than the upper limit value, it means that the execution stage R, which has not been executed, of the biopsy is present, that is, the biopsy is in progress. Therefore, the processing proceeds to step S20, and the controller 50 performs the control of projecting the Rn-relevant information associated with each of the next execution stage Rn, from the projector 40 toward the imaging surface of the imaging table 14.

In a case of the index n=2, since the execution stage transitions to the execution stage R2, in step S20, the controller 50 performs control of projecting R2-relevant information from the projector 40 toward the imaging surface of the imaging table 14.

The medical worker punctures the breast with the anesthetic needle from the opening portion 25 of the compression plate 18. Therefore, the controller 50 controls the projection unit 40A of the projector 40 to project the position M where the anesthetic needle is inserted and the depth to which the anesthetic needle is inserted, toward the imaging surface of the imaging table 14. The depth to which the anesthetic needle is inserted represents a distance from the epidermis of the breast to an injection position of the anesthetic solution along the Z direction, at the position M where the anesthetic needle is inserted.

Figure 9:
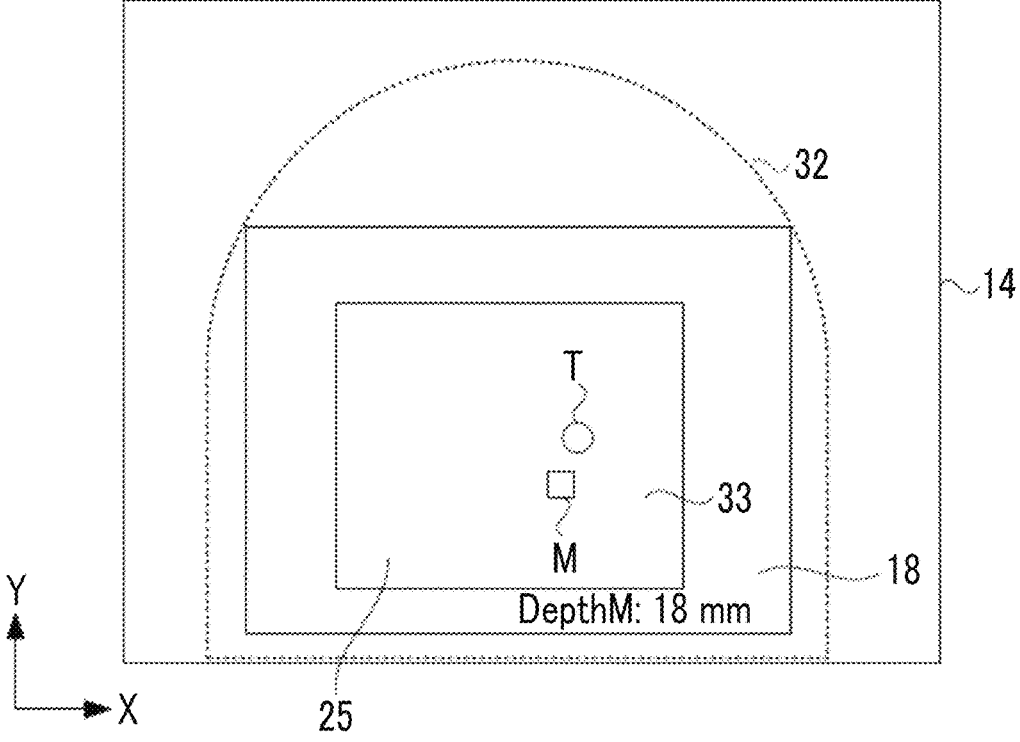
FIG. 9 is a diagram illustrating an example of R2-relevant information projected in an execution stage R2.

Note that the controller 50 may perform control of projecting the projection image including the position of the target T in addition to the position M where the anesthetic needle is inserted and the depth to which the anesthetic needle is inserted, from the projection unit 40A toward the imaging surface of the imaging table 14. As a result, as illustrated in FIG. 9, the position M where the anesthetic needle is inserted and the position of the target T are is displayed on the breast exposed through the opening portion 25 of the compression plate 18. In addition, the controller 50 may perform control of projecting the projection image including the skin line 32 from the projection unit 40A toward the imaging surface of the imaging table 14 such that the medical worker can check that the position of the breast has not deviated from the skin line 32.

There is no restriction on the display position of the depth to which the anesthetic needle is inserted, but in order to avoid overlapping with the display of the position M where the anesthetic needle is inserted and the position of the target T, it is preferable that the controller 50 displays the depth to which the anesthetic needle is inserted, at a location other than the breast exposed within the opening portion 25 of the compression plate 18. In the example illustrated in FIG. 9, the depth to which the anesthetic needle is inserted is displayed with an item name of "DepthM" on the compression plate 18.

In a case where two types of positions, that is, the position of the target T and the position M where the anesthetic needle is inserted, are displayed on the breast, it is preferable to change display forms of marks each indicating the position such that the medical worker can easily distinguish the positions. In the example illustrated in FIG. 9, the position of the target T is represented by a circle mark, and the position M where the anesthetic needle is inserted is represented by a square mark, but the display colors may be changed. In addition, the depth to which the anesthetic needle is inserted does not necessarily have to be represented numerically. For example, different colors may be associated in advance with each range of the depth to which the anesthetic needle is inserted, such as red for a depth of 0 mm or more and less than 5 mm and blue for a depth of 5 mm or more and less than 10 mm, and a color corresponding to the depth to which the anesthetic needle is inserted in the subject may be used as a color of the mark indicating the position M where the anesthetic needle is inserted.

The position M where the anesthetic needle is inserted and the depth to which the anesthetic needle is inserted are calculated by the controller 50 using, for example, the position of the target T and the compression force of the compression plate 18 on the breast. The reason why the compression force on the breast is considered in the calculation of the position M where the anesthetic needle is inserted and the depth to which the anesthetic needle is inserted is that the position of the target T may be changed depending on the degree of the compression force on the breast. The compression force on the breast is detected by, for example, a compression force detection sensor (not illustrated) provided in the mammography apparatus 2.

As described above, the position M where the anesthetic needle is inserted, the depth to which the anesthetic needle is inserted, the skin line 32, and the position of the target T are examples of the R2-relevant information associated with the execution stage R2. For example, in a case where the position M where the anesthetic needle is inserted is not displayed on the breast, the medical worker may perform anesthesia after marking the breast by puncturing the breast with the anesthesia needle by about 1 mm at a location considered to be the position M where the anesthesia needle is inserted such that the anesthesia needle is inserted into a desired position. However, in the mammography apparatus 2 of the present disclosure, since the R2-relevant information that is referred to in a case of performing the anesthesia in the execution stage R2 is displayed, the medical worker may puncture the specified position of the breast with the anesthetic needle, advance the anesthetic needle to the specified depth, and inject the anesthetic solution while referring to the R2-relevant information.

In a case where the execution stage R2 is completed, the medical worker notifies the mammography apparatus 2 of the transition instruction to perform transition to the next execution stage R, from the console 5 or the operation panel 29, for example. Since the next execution stage R is the biopsy needle position adjustment, for example, the mounting of the biopsy needle 21 on the lateral adapter 27 is the transition instruction.

In this case, the determination processing of step S30 in FIG. 7 is the affirmative determination, and the index n=3 is obtained by the processing of step S40. Since the index n is equal to or lower than the upper limit value, the determination processing of step S50 is the negative determination, and the processing proceeds to step S20.

In a case of the index n=3, since the execution stage transitions to the execution stage R3, in step S20, the controller 50 performs control of projecting R3-relevant information from the projector 40 toward the imaging surface of the imaging table 14.

Specifically, the controller 50 controls the projection unit 40A of the projector 40 to project the position of the target T in the XY plane toward the imaging surface of the imaging table 14. As a result, the position of the target T is displayed on the breast exposed through the opening portion 25 of the compression plate 18. Since the position of the target T in the XY plane is displayed on the breast, the medical worker does not have to check the position of the target T by looking at, for example, the examination image displayed on a display provided in the operation panel 29, for example. Therefore, the medical worker can check the position of the target T without diverting the visual line from the imaging surface of the imaging table 14.

In addition, the controller 50 controls the projection unit 40A of the projector 40 to project a depth of the target T in the breast along a direction (that is, the Z direction) orthogonal to the imaging surface of the imaging table 14, toward the imaging surface of the imaging table 14. In other words, the depth of the target T represents a distance from the position of a compression surface of the compression plate 18 that compresses the breast to the target T along the Z direction.

In addition, the controller 50 controls the projection unit 40A of the projector 40 to project a range that the distal end of the biopsy needle 21 can reach by adjusting the position of the biopsy needle 21 in the X direction and the Y direction, that is, a puncturable range 33, toward the imaging surface of the imaging table 14. There is no restriction on the display form of the puncturable range 33, and for example, the puncturable range 33 may be colored.

In a case where the target T is not included in the puncturable range 33, it means that the distal end of the biopsy needle 21 does not reach the target T even though the position of the biopsy needle 21 is adjusted, so that the biological tissue cannot be collected.

Therefore, the medical worker performs a treatment such as changing the attachment direction of the lateral adapter 27 to cause the target T to be included in the puncturable range 33. That is, on the basis of the positional relationship between the target T and the puncturable range 33, the medical worker can determine whether or not the biological tissue of the target T can be collected from the current attachment direction of the lateral adapter 27 before puncturing the breast with the biopsy needle 21. Therefore, there is no need to put, on the subject, a burden of changing the attachment direction of the adapter 27 and puncturing the breast again with the biopsy needle 21 due to the reason why the biological tissue of the target T cannot be collected in the current attachment direction of the lateral adapter 27 after puncturing the breast with the biopsy needle 21 in the execution stage R4 which is a subsequent execution stage R, for example.

Note that, in a case where the target T is not included in the puncturable range 33, the controller 50 may control the operation panel 29 to perform control of outputting, to the display of the operation panel 29, a warning that notifies the medical worker to adjust the position of the biopsy needle 21 by changing the attachment direction of the lateral adapter 27.

Figure 10:
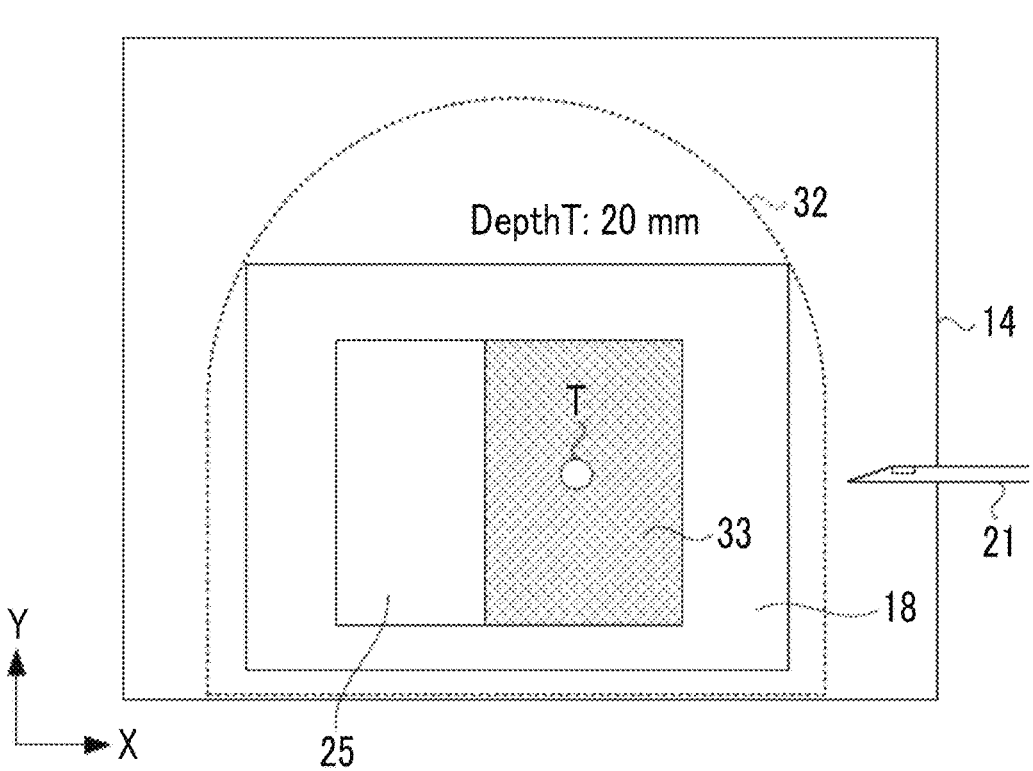
FIG. 10 is a diagram illustrating an example of R3-relevant information projected in an execution stage R3.

FIG. 10 is a diagram illustrating an example of the R3-relevant information projected from the projector 40 toward the imaging surface of the imaging table 14 in the execution stage R3. In FIG. 10, the depth of the target T is displayed with an item name of "DepthT" as an example. In addition, the target T is included in the puncturable range 33.

There is no restriction on the display positions of the depth of the target T as long as the display position is within the range of the imaging surface of the imaging table 14. However, as illustrated in FIG. 10, in order to avoid overlapping with the display of the position of the target T, it is preferable to display the depth of the target T at a location other than the breast that is exposed in the opening portion 25 of the compression plate 18. Specifically, the depth of the target T is displayed at any location of the compression plate 18, the imaging surface of the imaging table 14 on which the breast is not disposed, or the breast that protrudes to the outside of the compression plate 18 in a case where the compression plate 18 is viewed from above.

In addition, the controller 50 may perform control of projecting the projection image including the skin line 32 from the projection unit 40A toward the imaging surface of the imaging table 14 such that the medical worker can check that the position of the breast has not deviated from the skin line 32.

The medical worker operates the position adjustment mechanism of the lateral adapter 27 to adjust the position of the biopsy needle 21 such that the position of the distal end of the biopsy needle 21 in the Y direction in FIG. 10 is the same as the position of the target T in the Y direction while referring to the position of the target T. In addition, the medical worker operates the position adjustment mechanism of the lateral adapter 27 to adjust the position of the biopsy needle 21 such that the position of the distal end of the biopsy needle 21 in the Z direction orthogonal to the XY plane in FIG. 10 is the same as the position of the target T in the Z direction while referring to the depth of the target T.

In this case, the controller 50 may control the projection unit 40A of the projector 40 to project some marks toward the imaging surface of the imaging table 14 in a case where the Y coordinate value of the biopsy needle 21 is the same as the Y coordinate value of the target T and the Z coordinate value of the biopsy needle 21 is the same as the Z coordinate value of the target T. In a case where the medical worker adjusts the position of the biopsy needle 21 such that the mark is displayed, the positions of the distal end of the biopsy needle 21 in the Y direction and the Z direction are the same as the positions of the target T in the Y direction and the Z direction.

As described above, the position of the target T, the depth of the target T, the puncturable range 33, and the skin line 32 are examples of the R3-relevant information associated with the execution stage R3. In a case where the R3-relevant information is not displayed, the medical worker adjusts the position of the distal end of the biopsy needle 21 while imagining a positional relationship between the collection position of the biological tissue and the biopsy needle 21 in the head. However, in the mammography apparatus 2 of the present disclosure, since the R3-relevant information that is referred to in a case of adjusting the position of the biopsy needle 21 is displayed, the medical worker can adjust the position of the distal end of the biopsy needle 21 while visually checking the positional relationship between the collection position of the biological tissue and the biopsy needle 21.

In a case where the execution stage R3 is completed, the medical worker notifies the mammography apparatus 2 of the transition instruction to perform transition to the next execution stage R, from the console 5 or the operation panel 29, for example. Since the next execution stage R is the biopsy needle puncture, for example, the operation of the handle 27a of the lateral adapter 27 by the medical worker is the transition instruction.

In this case, the determination processing of step S30 in FIG. 7 is the affirmative determination, and the index n=4 is obtained by the processing of step S40. Since the index n is equal to or lower than the upper limit value, the determination processing of step S50 is the negative determination, and the processing proceeds to step S20.

In a case of the index n=4, since the execution stage transitions to the execution stage R4, in step S20, the controller 50 performs control of projecting R4-relevant information from the projector 40 toward the imaging surface of the imaging table 14.

Specifically, the controller 50 controls the projection unit 40A of the projector 40 to project the position of the target T in the XY plane toward the imaging surface of the imaging table 14. As a result, the position of the target T is displayed on the breast exposed through the opening portion 25 of the compression plate 18.

In addition, the controller 50 controls the projection unit 40A of the projector 40 to project a distance from the distal end of the biopsy needle 21 on the side that punctures the breast to the target T along a traveling direction of the biopsy needle 21 (in this case, the X direction because the puncture is performed in the lateral direction), to the imaging surface of the imaging table 14. The distance from the distal end of the biopsy needle 21 on the side that punctures the breast to the target T along the traveling direction of the biopsy needle 21 is referred to as a "target distance".

In addition, the controller 50 controls the projection unit 40A of the projector 40 to project the distance from the distal end of the biopsy needle 21 on the side that punctures the breast to the epidermis of the breast punctured by the biopsy needle 21, along the traveling direction of the biopsy needle 21, toward the imaging surface of the imaging table 14. The distance from the distal end of the biopsy needle 21 on the side that punctures the breast to the epidermis of the breast punctured by the biopsy needle 21 along the traveling direction of the biopsy needle 21 is referred to as a "biological distance". In a case where the biopsy needle 21 has entered the breast, the biological distance has a negative value.

The controller 50 may perform control of projecting the projection image including the skin line 32 from the projection unit 40A toward the imaging surface of the imaging table 14 such that the medical worker can check that the position of the breast has not deviated from the skin line 32.

In addition, the controller 50 can acquire the movement amount of the biopsy needle 21 along the X direction, which is measured by the displacement sensor provided in the lateral adapter 27, through the needle position controller 35. Therefore, the controller 50 updates the target distance and the biological distance that are changed as the biopsy needle 21 is moved by the medical worker operating the handle 27A, and performs the control of projecting the updated target distance and biological distance in real time toward the imaging surface of the imaging table 14.

After the biopsy needle 21 has reached the epidermis of the breast, in a case where the medical worker further moves the biopsy needle 21 toward the breast, the biopsy needle 21 enters the breast. Therefore, the medical worker moves the biopsy needle 21 while imagining the position of the biopsy needle 21. Therefore, the controller 50 controls the projection unit 40A of the projector 40 to perform the control of projecting the position of the biopsy needle 21 that has entered the breast, toward the imaging surface of the imaging table 14. Specifically, the controller 50 performs control of projecting an image (hereinafter, referred to as a "biopsy needle image G") of the biopsy needle 21 of the portion that has entered the breast, of the biopsy needle 21, from the projector 40 toward the imaging surface of the imaging table 14 in accordance with the position of the biopsy needle 21 in the breast. That is, the controller 50 performs control of updating the display position of the biopsy needle image G in real time in accordance with the movement of the biopsy needle 21. The controller 50 may determine whether or not the biopsy needle 21 has entered the breast by using, for example, the biological distance or the visible image captured by the camera 23.

The position of the biopsy needle 21 in the breast is estimated by the displacement sensor provided in the lateral adapter 27, but even in a case where there is no displacement sensor, the position of the biopsy needle 21 in the breast can be estimated. For example, in a case where the biopsy needle 21 is moved in the breast, the breast may bulge due to the biopsy needle 21 as the biopsy needle 21 is moved. Therefore, the controller 50 may execute known image recognition processing on the visible image captured by the camera 23 to extract a bulging portion of the breast, and estimate the position of the biopsy needle 21 in the breast.

Figure 11:
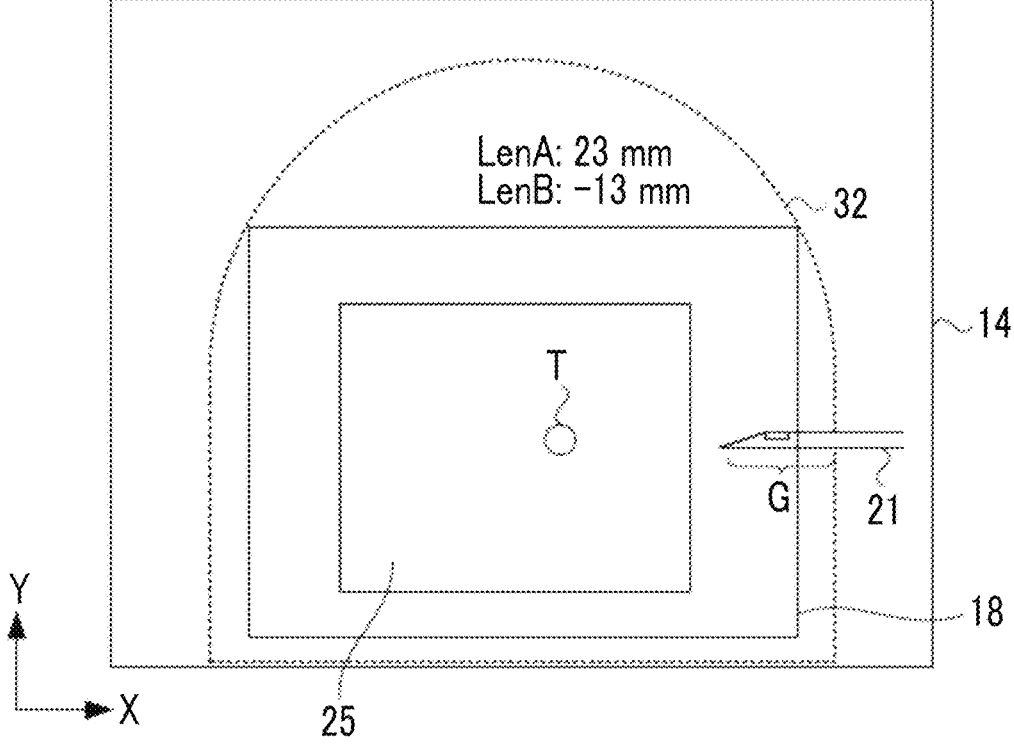
FIG. 11 is a diagram illustrating an example of R4-relevant information projected in an execution stage R4.

FIG. 11 is a diagram illustrating an example of a projection image in which the position of the biopsy needle 21 that has entered the breast is displayed as the biopsy needle image G. Since the position of the biopsy needle 21 that cannot be actually visually recognized is displayed by being superimposed on the breast, the medical worker does not have to operate the handle 27A while checking the gradations 27B of the lateral adapter 27. Therefore, the medical worker can move the distal end of the biopsy needle 21 to the position of the target T while referring to the position of the target T, the target distance, the biological distance, the biopsy needle image G, and the skin line 32 without diverting the visual line from the imaging surface of the imaging table 14, and can collect the biological tissue of the target T.

As described above, the position of the target T, the target distance, the biological distance, the biopsy needle image G, and the skin line 32 are examples of the R4-relevant information associated with the execution stage R4.

In a case where the execution stage R4 is completed, the medical worker notifies the mammography apparatus 2 of the transition instruction to perform transition to the next execution stage R, from the console 5 or the operation panel 29, for example. Since the next execution stage R is the biopsy needle removal, the execution of the operation of the handle 27A in a direction opposite to the operation direction of the handle 27A in the execution stage R4 is the transition instruction.

The transition instruction from the execution stage R4 to the execution stages R5 is not limited to this, and the controller 50 may determine, for example, that the transition instruction is given in a case where the distal end of the biopsy needle 21 appears on the outside of the breast. In addition, the controller 50 may determine that the transition instruction is given in a case where the handle 27A is operated in the direction opposite to the operation direction in the execution stage R4 and is moved in the opposite direction along the X direction by a predetermined distance (referred to as a "specified distance") from the position of the target T. The specified distance can be changed by the medical worker, and is stored in, for example, the storage unit 50B.

In this case, the determination processing of step S30 in FIG. 7 is the affirmative determination, and the index n=5 is obtained by the processing of step S40. Since the index n is equal to or lower than the upper limit value, the determination processing of step S50 is the negative determination, and the processing proceeds to step S20.

In a case of the index n=5, since the execution stage transitions to the execution stage R5, in step S20, the controller 50 performs control of projecting R5-relevant information from the projector 40 toward the imaging surface of the imaging table 14.

Specifically, the controller 50 controls the projection unit 40A of the projector 40 to project the elapsed time from the pulling out of the biopsy needle 21 from the breast, toward the imaging surface of the imaging table 14.

After the biopsy needle 21 is pulled out, the medical worker stops the blood flowing out from the needle pulling-out location, but the time until the hemostasis is performed is important. In the mammography apparatus 2, since the elapsed time from the pulling out of the biopsy needle 21 is displayed, the medical worker does not have to activate a timer while pulling out the biopsy needle 21, and the convenience is improved.

Figure 12:
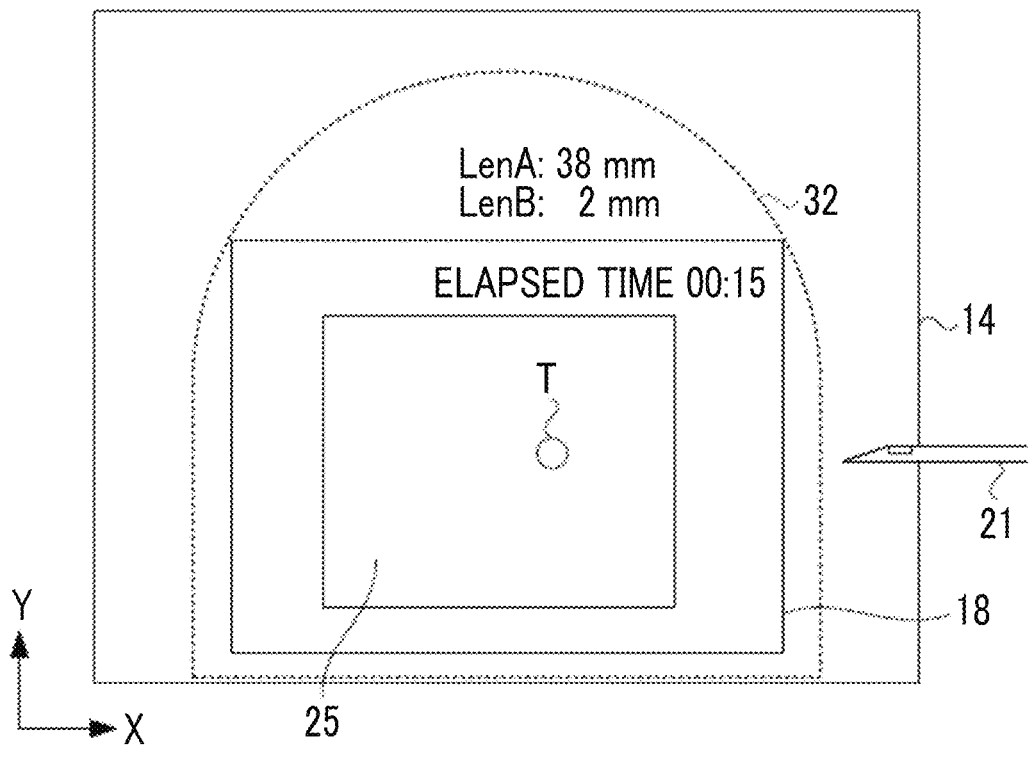
FIG. 12 is a diagram illustrating an example of R5-relevant information projected in an execution stage R5.

FIG. 12 is a diagram illustrating an example of the projection image including the elapsed time from the pulling out of the biopsy needle 21 from the breast. In FIG. 12, the time displayed together with the item name of "elapsed time" represents the elapsed time from the pulling out of the biopsy needle 21 from the breast. Note that there is no restriction on the display position of the elapsed time, and the elapsed time may be displayed at any position within the range of the imaging surface of the imaging table 14.

The elapsed time from the pulling out of the biopsy needle 21 from the breast is the elapsed time from the reception of the transition instruction to the execution stage R5. Therefore, in a case where the operation of the handle 27A in the direction opposite to the operation direction of the handle 27A in the execution stage R4 is set as the transition instruction to the execution stage R5, the time from the start of the movement of the biopsy needle 21 in a direction away from the target T is displayed as the elapsed time. In a case where the appearance of the distal end of the biopsy needle 21 on the outside of the breast is set as the transition instruction to the execution stage R5, the time from the appearance of the distal end of the biopsy needle 21, which has been inserted into the breast, on the outside of the breast is displayed as the elapsed time. In addition, in a case where the fact that the handle 27A is operated in the direction opposite to the operation direction in the execution stage R4 and is moved from the position of the target T only by the specified distance in the opposite direction along the X direction is set as the transition instruction to the execution stage R5, the time from the distal end of the biopsy needle 21 being separated from the target T by the specified distance along the X direction after collecting the biological tissue of the target T is displayed as the elapsed time.

Note that the controller 50 may perform control of projecting the projection image including the skin line 32 from the projection unit 40A toward the imaging surface of the imaging table 14 such that the medical worker can check that the position of the breast has not deviated from the skin line 32.

In addition, in order to clearly indicate the positional relationship of the biopsy needle 21, the controller 50 may perform the control of projecting the projection image including the position of the target T, the biopsy needle image G, the target distance, and the biological distance, from the projection unit 40A toward the imaging surface of the imaging table 14.

As described above, the elapsed time, the position of the target T, the target distance, the biological distance, the biopsy needle image G, and the skin line 32 are examples of the R5-relevant information associated with the execution stage R5.

In a case where the execution stage R5 is completed, the medical worker notifies the mammography apparatus 2 of an end instruction to end the biopsy, from the console 5 or the operation panel 29, for example. The end instruction is an example of the transition instruction for transitioning to end processing of the biopsy.

In this case, the determination processing of step S30 in FIG. 7 is the affirmative determination, and the index n=6 is obtained by the processing of step S40. Since the index n exceeds the upper limit value, the determination processing of step S50 is the affirmative determination, and the controller 50 ends the biopsy support processing illustrated in FIG. 7. With the end of the biopsy support processing, the controller 50 stops the projection of the projection image by the projector 40, controls the compression plate moving mechanism 19 to move the compression plate 18 toward the radiation irradiator 17, and releases the compression on the breast.

As described above, with the mammography apparatus 2 according to the present disclosure, for each execution stage R of the biopsy, the relevant information associated with the technique performed by the medical worker in each execution stage R is projected from the projector 40 toward the imaging surface of the imaging table 14. Therefore, the medical worker can easily perform the technique, and the execution accuracy of the biopsy is improved, as compared with a case where information which is not relevant to the technique performed by the medical worker in each execution stage R is also displayed.

Note that, in the execution stage R2 to the execution stage R4, the controller 50 may include the position of the blood vessel and the position of the mammary gland in the R2-relevant information to the R4-relevant information in order to prevent the blood vessel and the mammary gland from being punctured with the anesthetic needle and the biopsy needle 21. That is, the controller 50 may perform control of projecting the projection image including the position of the blood vessel and the position of the mammary gland, from the projection unit 40A toward the imaging surface of the imaging table 14. The controller 50 may specify the position of the blood vessel and the position of the mammary gland included in the projection image in advance from the examination image using, for example, known image recognition processing.

In addition, in the biopsy support processing illustrated in FIG. 7, in step S40, the controller 50 increases the index n one by one, but a value corresponding to the content of the transition instruction received by the controller 50 may be set as the index n. For example, in a case where the operation of the handle 27A of the lateral adapter 27 is received, the controller 50 sets "4" as the index n, and transitions to the execution stage R4. In addition, the medical worker may set the value of the index n. In this way, for example, in a case where the medical worker determines that the anesthesia is not necessary in the execution stage R2, the mammography apparatus 2 can display the relevant information according to the procedure of the medical worker such that the mammography apparatus 2 displays the R1-relevant information and then displays the R3-relevant information without displaying the R2-relevant information.

Although one embodiment of the medical image acquisition apparatus 1 has been described using the embodiment, the form of the disclosed medical image acquisition apparatus 1 is an example, and the form of the medical image acquisition apparatus 1 is not limited to the scope described in the embodiment. Various modifications and improvements can be added to the embodiments without departing from the scope of the present disclosure, and the embodiments to which the modifications or improvements are added are also included in the technical scope of the present disclosure.

For example, the internal processing order in the flowchart of the biopsy support processing illustrated in FIG. 7 may be changed without departing from the scope of the present disclosure.

In the embodiments, for example, a form in which the biopsy support processing illustrated in FIG. 7 is implemented by software processing has been described. On the other hand, processing equivalent to the flowchart of the biopsy support processing may be performed by hardware. In this case, the processing speed can be increased as compared with a case where the biopsy support processing is implemented by software processing.

In the above-described embodiment, the processor refers to a processor in a broad sense, and examples of the processor include a general-purpose processor (for example, the CPU 50A), and a dedicated processor (for example, a graphics processing unit (GPU), an application specific integrated circuit (ASIC), a field programmable gate array (FPGA), a programmable logic device, or the like).

In addition, the operation of the processor in the embodiment described above may be performed not only by one processor but also by cooperation of a plurality of processors provided at physically separated positions. In addition, the order of the operations of the processor is not limited to only the order described in the embodiments, and may be changed as appropriate.

In the embodiment described above, an example in which the control program 56 is stored in the storage unit 50B has been described. However, the storage destination of the control program 56 is not limited to the storage unit 50B. The control program 56 of the present disclosure can also be provided by being recorded in a computer-readable storage medium.

For example, the control program 56 may be provided by being recorded on an optical disk, such as a compact disk read only memory (CD-ROM), a digital versatile disk read only memory (DVD-ROM), and a blue ray disk. In addition, the control program 56 may be provided by being recorded in a portable semiconductor memory such as a universal serial bus (USB) memory and a memory card. The storage unit 50B, the CD-ROM, the DVD-ROM, the blue ray disk, the USB, and the memory card are examples of the non-transitory storage medium.

Further, the controller 50 may download the control program 56 from an external apparatus connected to the communication line through the I/F unit 59, and store the downloaded control program 56 in the storage unit 50B of the controller 50. In this case, the CPU 50A of the controller 50 reads the control program 56 downloaded from the external apparatus, from the storage unit 50B to execute the biopsy support processing.

Hereinafter, supplementary notes according to the present embodiment will be described.

(Supplementary Note 1)

A medical image acquisition apparatus comprising:

a biopsy apparatus;

an imaging table that is used to capture an image of a living body disposed on an imaging surface with an imaging apparatus;

a projector that projects the image; and at least one processor, wherein the processor performs control of projecting relevant information associated with each execution stage of a biopsy that is performed on the living body using the biopsy apparatus, from the projector toward the imaging surface of the imaging table for each execution stage.

(Supplementary Note 2)

The medical image acquisition apparatus according to Supplementary Note 1, wherein, in a case where the execution stage of the biopsy is an arrangement stage in which the living body is disposed on the imaging surface of the imaging table, the processor performs control of projecting the disposing position of the living body on the imaging surface of the imaging table and a collection position where a biological tissue is collected from the living body, from the projector toward the imaging surface of the imaging table.

(Supplementary Note 3)

The medical image acquisition apparatus according to Supplementary Note 2, wherein, on the basis of a difference in spreading manners of the living body on the imaging surface of the imaging table due to a difference between a type and a compression force of a first compression plate, which is a plate used in a case of capturing an examination image of the living body using the imaging apparatus before the biopsy in order to check the collection position and compresses the living body against the imaging surface of the imaging table, and a type and a compression force of a second compression plate, which is a plate used for the biopsy, has an opening portion on a surface facing the imaging surface of the imaging table, and compresses the living body against the imaging surface of the imaging table, the processor performs control of projecting a disposing position of the living body which is adjusted such that the collection position comes to a center of the opening portion of the second compression plate, from the projector toward the imaging surface of the imaging table.

(Supplementary Note 4)

The medical image acquisition apparatus according to Supplementary Note 3, wherein, in a case where the living body is disposed at the disposing position of the living body which is adjusted such that the collection position comes to the center of the opening portion of the second compression plate and a contour portion of the living body enters the opening portion of the second compression plate, the processor performs control of projecting the disposing position of the living body which is adjusted such that the contour portion of the living body does not enter the opening portion and the collection position is within a range of the opening portion of the second compression plate, from the projector toward the imaging surface of the imaging table.

(Supplementary Note 5)

The medical image acquisition apparatus according to Supplementary Note 3 or 4, wherein, in a case where there are a plurality of collection positions, the processor performs control of projecting the disposing position of the living body which is adjusted such that each of the collection positions is within a range of the opening portion of the second compression plate, from the projector toward the imaging surface of the imaging table.

(Supplementary Note 6)

The medical image acquisition apparatus according to Supplementary Note 1, wherein, in a case where the execution stage of the biopsy is a pre-treatment stage where anesthesia is performed on the living body, the processor performs control of further projecting information regarding a position where an anesthetic needle is inserted and a depth to which the anesthetic needle is inserted along a direction intersecting the imaging surface of the imaging table, from the projector toward the imaging surface of the imaging table.

(Supplementary Note 7)

The medical image acquisition apparatus according to Supplementary Note 1, wherein, in a case where the execution stage of the biopsy is a puncturing stage in which the living body is punctured with a biopsy needle attached to the biopsy apparatus along the imaging surface of the imaging table, the processor performs control of projecting a position of the biopsy needle, a collection position where a biological tissue is collected from the living body, and a distance from a distal end of the biopsy needle to the collection position, from the projector toward the imaging surface of the imaging table.

(Supplementary Note 8)

The medical image acquisition apparatus according to Supplementary Note 7, wherein the processor performs control of projecting the position of the biopsy needle in accordance with a motion of the biopsy needle, from the projector toward the imaging surface of the imaging table.

(Supplementary Note 9)

The medical image acquisition apparatus according to Supplementary Note 1, wherein the execution stage of the biopsy is a needle removal stage in which the biopsy needle inserted to the living body is pulled out from the living body, the processor performs control of projecting an elapsed time from the pulling out of the biopsy needle from the living body, from the projector toward the imaging surface of the imaging table.

(Supplementary Note 10)

The medical image acquisition apparatus according to Supplementary Note 9, wherein the processor performs control of projecting an elapsed time from a distal end of the biopsy needle that has punctured the living body, being separated from a collection position where a biological tissue of the living body is collected, by a predetermined distance, from the projector toward the imaging surface of the imaging table.

(Supplementary Note 11)

The medical image acquisition apparatus according to Supplementary Note 9, wherein the processor performs control of projecting an elapsed time from a distal end of the biopsy needle that has punctured the living body, appearing on an outside of the living body, from the projector toward the imaging surface of the imaging table.

(Supplementary Note 12)

A mammography apparatus comprising:

the medical image acquisition apparatus according to any one of Supplementary Notes 1 to 11, wherein the imaging apparatus is a radiography apparatus that captures a radiation image of the living body by irradiating the living body with radiation, and the living body is a breast.

(Supplementary Note 13)

A control program executed in a medical image acquisition apparatus including a biopsy apparatus, an imaging table that is used to capture an image of a living body disposed on an imaging surface with an imaging apparatus, a projector that projects the image, and at least one processor, the control program for causing a computer to execute processing of performing control of projecting relevant information associated with each execution stage of a biopsy that is performed on the living body using the biopsy apparatus, from the projector toward the imaging surface of the imaging table for each execution stage.

EXPLANATION OF REFERENCES

1: medical image acquisition apparatus
2: mammography apparatus
3: image storage system
4: radiography system
5: console
6: RIS
7: bus of image storage system
8: bus of console
9: bus of mammography apparatus
11: base
12: C-axis
13: arm
14: imaging table
15: radiation detector
16: radiation accommodation portion
17: radiation irradiator
18: compression plate
19: compression plate moving mechanism
20: support portion
21: biopsy needle
22: biopsy needle unit
23: camera
24: moving mechanism
25: opening portion of compression plate
26: biopsy unit
27: lateral adapter
27A: handle
27B: gradations
28: operating part
29: operation panel
30: radiation source 31: arm controller
32: skin line
33: puncturable range
34: compression plate controller
35: needle position controller
40: projector
40A: projection unit of projector
40B: power supply unit of projector
50: controller of mammography apparatus
50A: CPU of mammography apparatus
50B: storage unit of mammography apparatus
50C: RAM of mammography apparatus
56: control program
59: I/F unit of mammography apparatus
60: controller of console
60A: CPU of console
60B: storage unit of console
60C: RAM of console
61: output unit
62: operating part
69: I/F unit of console
70: controller of image storage system
70A: CPU of image storage system
70B: storage unit of image storage system
70C: RAM of image storage system
79: I/F unit of image storage system
G: biopsy needle image
M: position where anesthetic needle is inserted
R: execution stage of biopsy
R1: execution stage of positioning
R2: execution stage of anesthesia
R3: execution stage of biopsy needle position adjustment
R4: execution stage of biopsy needle puncture
R5: execution stage of biopsy needle removal
T: target
n: index

What is claimed is:

1. A medical image acquisition apparatus comprising:
a biopsy apparatus;
an imaging table that is used to capture an image of a living body disposed on an imaging surface with an imaging apparatus;
a projector that projects the image; and
at least one processor,
wherein the processor performs control of projecting relevant information associated with each execution stage of a biopsy that is performed on the living body using the biopsy apparatus, from the projector toward the imaging surface of the imaging table for each execution stage.

2. The medical image acquisition apparatus according to claim 1, wherein, in a case where the execution stage of the biopsy is an arrangement stage in which the living body is disposed on the imaging surface of the imaging table, the processor performs control of projecting a disposing position of the living body on the imaging surface of the imaging table and a collection position where a biological tissue is collected from the living body, from the projector toward the imaging surface of the imaging table.

3. The medical image acquisition apparatus according to claim 2, wherein, on the basis of a difference in spreading manners of the living body on the imaging surface of the imaging table due to a difference between a type and a compression force of a first compression plate, which is a plate used in a case of capturing an examination image of the living body using the imaging apparatus before the biopsy in order to check the collection position and compresses the living body against the imaging surface of the imaging table, and a type and a compression force of a second compression plate, which is a plate used for the biopsy, has an opening portion on a surface facing the imaging surface of the imaging table, and compresses the living body against the imaging surface of the imaging table, the processor performs control of projecting the disposing position of the living body which is adjusted such that the collection position comes to a center of the opening portion of the second compression plate, from the projector toward the imaging surface of the imaging table.

4. The medical image acquisition apparatus according to claim 3, wherein, in a case where the living body is disposed at the disposing position of the living body which is adjusted such that the collection position comes to the center of the opening portion of the second compression plate and a contour portion of the living body enters the opening portion of the second compression plate, the processor performs control of projecting the disposing position of the living body which is adjusted such that the contour portion of the living body does not enter the opening portion and the collection position is within a range of the opening portion of the second compression plate, from the projector toward the imaging surface of the imaging table.

5. The medical image acquisition apparatus according to claim 3, wherein, in a case where there are a plurality of collection positions, the processor performs control of projecting the disposing position of the living body which is adjusted such that each of the collection positions is within a range of the opening portion of the second compression plate, from the projector toward the imaging surface of the imaging table.

6. The medical image acquisition apparatus according to claim 1, wherein, in a case where the execution stage of the biopsy is a pre-treatment stage where anesthesia is performed on the living body, the processor performs control of further projecting information regarding a position where an anesthetic needle is inserted and a depth to which the anesthetic needle is inserted along a direction intersecting the imaging surface of the imaging table, from the projector toward the imaging surface of the imaging table.

7. The medical image acquisition apparatus according to claim 1, wherein, in a case where the execution stage of the biopsy is a puncturing stage in which the living body is punctured with a biopsy needle attached to the biopsy apparatus along the imaging surface of the imaging table, the processor performs control of projecting a position of the biopsy needle, a collection position where a biological tissue is collected from the living body, and a distance from a distal end of the biopsy needle to the collection position, from the projector toward the imaging surface of the imaging table.

8. The medical image acquisition apparatus according to claim 7, wherein the processor performs control of projecting the position of the biopsy needle in accordance with a motion of the biopsy needle, from the projector toward the imaging surface of the imaging table.

9. The medical image acquisition apparatus according to claim 1, wherein the execution stage of the biopsy is a needle removal stage in which a biopsy needle that has punctured the living body is pulled out from the living body, the processor performs control of projecting an elapsed time from the pulling out of the biopsy needle from the living body, from the projector toward the imaging surface of the imaging table.

10. The medical image acquisition apparatus according to claim 9, wherein the processor performs control of projecting an elapsed time from a distal end of the biopsy needle that has punctured the living body, being separated from a collection position where a biological tissue of the living body is collected, by a predetermined distance, from the projector toward the imaging surface of the imaging table.

11. The medical image acquisition apparatus according to claim 9, wherein the processor performs control of projecting an elapsed time from a distal end of the biopsy needle that has punctured the living body, appearing on an outside of the living body, from the projector toward the imaging surface of the imaging table.

12. A mammography apparatus comprising:

the medical image acquisition apparatus according to claim 1, wherein the imaging apparatus is a radiography apparatus that captures a radiation image of the living body by irradiating the living body with radiation, and the living body is a breast.

13. A non-transitory computer readable medium storing a control program executed in a medical image acquisition apparatus including a biopsy apparatus, an imaging table that is used to capture an image of a living body disposed on an imaging surface with an imaging apparatus, a projector that projects the image, and at least one processor, the control program for causing a computer to execute processing of performing control of projecting relevant information associated with each execution stage of a biopsy that is performed on the living body using the biopsy apparatus, from the projector toward the imaging surface of the imaging table for each execution stage.

\* \* \* \* \*